United States Patent
Oberholzer et al.

(10) Patent No.: US 9,657,271 B2
(45) Date of Patent: May 23, 2017

(54) METHOD OF ISOLATING CELLS FROM A TISSUE IN A MAMMAL

(71) Applicants: Hemoglobin Oxygen Therapeutics LLC, Souderton, PA (US); The Board of Trustees of the University of Illinois, Urbana, IL (US)

(72) Inventors: Jose Oberholzer, Winnetka, IL (US); Marc Doubleday, Cary, IL (US)

(73) Assignees: The Board of Trustees of the University of Illinois, Urbana, IL (US); Hemoglobin Oxygen Therapeutics LLC, Souderton, PA (US)

( * ) Notice: Subject to any disclaimer, the term of this patent is extended or adjusted under 35 U.S.C. 154(b) by 561 days.

(21) Appl. No.: 13/755,091

(22) Filed: Jan. 31, 2013

(65) Prior Publication Data
US 2013/0316455 A1    Nov. 28, 2013

Related U.S. Application Data

(60) Continuation of application No. 13/041,685, filed on Mar. 7, 2011, now abandoned, which is a continuation of application No. 11/626,727, filed on Jan. 24, 2007, now abandoned, application No. 13/755,091, filed on Jan. 31, 2013, which is a continuation of application No. 13/016,758, filed on Jan. 28, 2011, now abandoned, which is a division of application No. 12/161,542, filed as application No. PCT/US2007/060987 on Jan. 24, 2007, now abandoned.

(60) Provisional application No. 60/761,663, filed on Jan. 24, 2006, provisional application No. 60/761,663, filed on Jan. 24, 2006.

(51) Int. Cl.
| | | |
|---|---|---|
| *C12N 5/071* | (2010.01) | |
| *A01N 1/02* | (2006.01) | |
| *A61K 38/42* | (2006.01) | |
| *A61K 38/48* | (2006.01) | |
| *A61K 35/39* | (2015.01) | |

(52) U.S. Cl.
CPC ............. *C12N 5/0676* (2013.01); *A01N 1/02* (2013.01); *A01N 1/0226* (2013.01); *A61K 35/39* (2013.01); *A61K 38/42* (2013.01); *A61K 38/482* (2013.01); *A61K 38/4886* (2013.01)

(58) Field of Classification Search
None
See application file for complete search history.

(56) References Cited

U.S. PATENT DOCUMENTS

| | | |
|---|---|---|
| 4,001,200 A | 1/1977 | Bonsen et al. |
| 4,001,401 A | 1/1977 | Bonsen et al. |
| 4,049,673 A | 9/1977 | Scheinberg |
| 4,053,590 A | 10/1977 | Bonsen et al. |
| 4,061,736 A | 12/1977 | Morris et al. |
| 4,113,853 A | 9/1978 | Funakoshi et al. |
| 4,136,093 A | 1/1979 | Bonhard et al. |
| 4,140,162 A | 2/1979 | Gajewski et al. |
| 4,460,365 A | 7/1984 | Ganshirt et al. |
| 4,485,174 A | 11/1984 | Chaing et al. |
| 4,526,715 A | 7/1985 | Koke et al. |
| 4,529,719 A | 7/1985 | Tye |
| 4,538,981 A | 9/1985 | Venturini |
| 4,561,110 A | 12/1985 | Herbert |
| 4,650,786 A | 3/1987 | Wong |
| 4,670,417 A | 6/1987 | Iwasaki et al. |
| 4,699,816 A | 10/1987 | Galli |
| 4,704,402 A | 11/1987 | Abraham et al. |
| 4,711,852 A | 12/1987 | Jacobson et al. |
| 4,761,209 A | 8/1988 | Bonaventure et al. |
| 4,826,811 A | 5/1989 | Sehgal et al. |
| 4,826,955 A | 5/1989 | Akkapeddi et al. |
| 4,835,097 A | 5/1989 | Sauders |
| 4,857,636 A | 8/1989 | Hsia |
| 4,861,867 A | 8/1989 | Estep |
| 4,988,515 A | 1/1991 | Buckberg |
| 5,028,588 A | 7/1991 | Hoffman et al. |

(Continued)

FOREIGN PATENT DOCUMENTS

| | | |
|---|---|---|
| EP | 0361720 | 4/1990 |
| GB | 2107191 | 8/1984 |

(Continued)

OTHER PUBLICATIONS

Kim et al., Improved phenotype of rat islets in a macrocapsule by co-encapsulation with cross-linked Hb, J. Biomater. Sci. Polymer Edn., vol. 16, No. 12, pp. 1521-1535, 2005.*
Avila et al., Improvement of Pancreatic Islet Isolation Outcomes Using Glutamine Perfusion During Isolation Procedure, Cell Transplantation, vol. 12, pp. 877-881, 2003.*
Avila-AJT, Avila et al., Intra-Ductal Glutamine Administration Reduces Oxidative Injury During Human Pancreatic Islet Isolation, American Journal of Transplantation, 2005: 5:2830-2837.*
Matsumoto et al., Effect of the Two-Layer method of pancreas preservation on human iselt isolation, as assessed by the Edmonton Isolation protocol, Transplantation, vol. 74, 1414-1419, No. 10,Nov. 27, 2002.*

(Continued)

*Primary Examiner* — Taeyoon Kim
*Assistant Examiner* — Srikanth Patury
(74) *Attorney, Agent, or Firm* — Hamilton, Brook, Smith & Reynolds, P.C.

(57) ABSTRACT

Solutions and suspensions comprising polymerized hemoglobin derived from human blood are disclosed. The solutions and suspensions may comprise cell culture medium, an enzyme (such as a protease), and/or a buffer. Processes of preparing the solutions and suspensions are also disclosed. The solutions and suspensions may be employed in methods of isolating mammalian cells, such as pancreatic islets, methods of preserving mammalian tissue and organs, methods of aiding the recovery of mammalian cells following their isolation, methods of maintaining mammalian cells, methods of propagating mammalian cells, and methods of treating a mammal with diabetes.

16 Claims, 10 Drawing Sheets

(56) References Cited

U.S. PATENT DOCUMENTS

| | | |
|---|---|---|
| 5,045,529 A | 9/1991 | Chiang |
| 5,051,353 A | 9/1991 | Stratton et al. |
| 5,061,688 A | 10/1991 | Beissinger et al. |
| 5,084,558 A | 1/1992 | Rausch et al. |
| 5,100,401 A | 3/1992 | Patel |
| 5,167,657 A | 12/1992 | Patel |
| 5,178,884 A | 1/1993 | Goodrich et al. |
| 5,189,146 A | 2/1993 | Hsia |
| 5,194,590 A | 3/1993 | Sehgal et al. |
| 5,206,075 A | 4/1993 | Hodgson, Jr. |
| 5,217,648 A | 6/1993 | Beissinger et al. |
| 5,234,903 A | 8/1993 | Nho et al. |
| 5,241,031 A | 8/1993 | Mehta |
| 5,264,555 A | 11/1993 | Shorr et al. |
| 5,272,236 A | 12/1993 | Lai et al. |
| 5,278,272 A | 1/1994 | Lai et al. |
| 5,296,465 A | 3/1994 | Rausch et al. |
| 5,296,466 A | 3/1994 | Kilbourn et al. |
| 5,334,706 A | 8/1994 | Przybelski |
| 5,352,773 A | 10/1994 | Kandler et al. |
| 5,356,709 A | 10/1994 | Woo et al. |
| 5,380,824 A | 1/1995 | Marschall et al. |
| 5,438,041 A | 8/1995 | Zheng et al. |
| 5,439,882 A | 8/1995 | Feola et al. |
| 5,464,814 A | 11/1995 | Sehgal et al. |
| 5,683,768 A | 11/1997 | Shang et al. |
| 5,691,452 A | 11/1997 | Gawryl |
| 5,691,453 A | 11/1997 | Wertz et al. |
| 5,695,840 A | 12/1997 | Mueller |
| 5,747,649 A | 5/1998 | Sehgal et al. |
| 5,789,376 A | 8/1998 | Hsia |
| 5,840,852 A | 11/1998 | Rausch et al. |
| 5,895,810 A | 4/1999 | Light et al. |
| 5,929,031 A | 7/1999 | Kerwin et al. |
| 5,955,581 A | 9/1999 | Rausch et al. |
| 5,988,422 A | 11/1999 | Vallot |
| 5,998,361 A | 12/1999 | Bucci et al. |
| 6,027,776 A | 2/2000 | Mueller |
| 6,076,457 A | 6/2000 | Vallot |
| 6,127,043 A | 10/2000 | Lange |
| 6,133,425 A | 10/2000 | Sehgal et al. |
| 6,150,507 A | 11/2000 | Houtchens et al. |
| 6,271,351 B1 | 8/2001 | Gawryl |
| 6,288,027 B1 | 9/2001 | Gawryl et al. |
| 6,323,320 B1 | 11/2001 | Sehgal et al. |
| 6,498,141 B2* | 12/2002 | DeWoskin et al. .......... 514/13.4 |
| 6,498,142 B1 | 12/2002 | Sampath et al. |
| 6,506,599 B1 | 1/2003 | Yoon |
| 6,552,173 B2 | 4/2003 | Sehgal et al. |
| 6,696,238 B2 | 2/2004 | Murphy et al. |
| 6,747,132 B2 | 6/2004 | Privalle et al. |
| 6,914,127 B2 | 7/2005 | Sehgal et al. |
| 7,135,553 B2 | 11/2006 | Avella et al. |
| 7,202,341 B2 | 4/2007 | McGinnis et al. |
| 7,291,592 B2 | 11/2007 | Gould et al. |
| 7,411,044 B2 | 8/2008 | Avella et al. |
| 7,435,795 B2 | 10/2008 | McGinnis et al. |
| 7,521,417 B2 | 4/2009 | DeWoskin et al. |
| 2002/0025343 A1 | 2/2002 | Dewoskin et al. |
| 2002/0065211 A1 | 5/2002 | Jacobs, Jr. et al. |
| 2002/0172665 A1 | 11/2002 | Rosenberg |
| 2004/0186047 A1 | 9/2004 | Avella et al. |
| 2007/0196810 A1 | 8/2007 | Doubleday |
| 2009/0004159 A1 | 1/2009 | Oberholzer |
| 2011/0142808 A1 | 6/2011 | Oberholzer |
| 2011/0200981 A1 | 8/2011 | Doubleday |
| 2013/0095467 A1 | 4/2013 | Doubleday |
| 2013/0316455 A1 | 11/2013 | Oberholzer et al. |

FOREIGN PATENT DOCUMENTS

| | | |
|---|---|---|
| JP | 2009-524436 | 7/2009 |
| WO | WO 89/12456 | 12/1989 |
| WO | WO 92/02239 | 2/1992 |
| WO | WO 97/35883 | 10/1997 |
| WO | WO 96/29346 | 4/1999 |
| WO | WO 99/18979 | 4/1999 |
| WO | WO 00/21366 | 4/2000 |
| WO | WO 01/01775 | 1/2001 |
| WO | WO 01/01921 | 1/2001 |
| WO | WO 02/089571 | 11/2002 |
| WO | WO 2004/066953 | 8/2004 |
| WO | WO 2007/087570 A2 | 8/2007 |

OTHER PUBLICATIONS

Docherty, et al., "Identification of a 31,5000 molecular weight islet cell protease as cathepsin B," *Proc. Natl. Acad. Sci.*, 80: 3245-3249 (1983).

Avila, et al., "Improved Outcomes in Islet Isolation and Transplantation by the Use of a Novel Hemoglobin-based O2 Carrier," *American J. Transplantation*, 6(12): 2861-2870 (2006).

Ortegon, et al., "The polymerized bovine hemoglobin-based oxygen-carrying solution (HBOC-201) is not toxic to neural cells in culture," *J. Trauma, Injury, Infection and Critical Care*, 53(6): 1068-1072 (2002), abstract only.

Schwartz, J.P., et al., "The Influence of Coronary Stenosis on Transfusion Need.," *Cardiothoracic Surgery*, Surgical Forum XLIV: 226-228 (1993).

Moss, G.S., et al., "Transport of Oxygen and Carbon Dioxide by Hemoglobin-Saline Solution in the Red Cell-Free Primate," *Surg. Gynecol Obstet*, 142: 357-362 (Mar. 1976).

Frantantoni, J.C., "Points to consider on efficacy evaluation of hemoglobin and perfluorocarbon based oxygen carriers," *Transfusion*, 34(8): 712-713 (1994).

Frantantoni, J.C., "Red Cell Subsitutes: Evolution of Approaches for Demonstrating Efficacy, Blood-substitutes—Present and Future Perspectives," *Elsevier Science S.A.*, p. 33-39 (1998).

Friedman, et al, "In vivo evaluation of pyridoxalated-polymerized hemoglobin solution," cited in *Biol. Abstracts*, 79(5): AB-720, Abstract No. 43028 (1984).

Klein, "Specific binding of hemoglobin on agarose-linked haptoglobin," cited in *Chem. Abstracts*, vol. 79: Abstract No. 39807z (1973).

"Film Preserves Blood Substitute," *Pharmaceutical & Medical Packaging News*, Jul. 1998.

"Improved Barrier: Longer Life for Lifesaving Blood Product," *Packaging World*, p. 70, Sep. 1998.

DeVenuto, et al., "Preparation and Evaluation of Pyridoxalated Polymerized Human Hemoglobin," *Journal of Surgical Research*, 34: 205-212 (1983).

DeVenuto, et al., "Characteristics of Stroma-free Hemoglobin Prepared by Crystallization," *J. Lab. Clin. Med*, 89: 509-516 (1977).

Devenuto, F., "Hemoglobin Solutions as Oxygen-Delivering Resuscitation Fluids," 10: 238-245 (1982).

DeVenuto, F., "Modified Hemoglobin Solution as a Resuscitation Fluid," *Vox Sang*, 44: 129-142 (1983).

Sehgal, et al., "Preparation and in vitro Characteristics of Polymerized Pyridoxylated Hemoglobin," *Transfusion*, 23: 158-162 (1983).

Berger, et al., "Achieving Efficacy and Sterility in Flexible Packaging," *Medical Device & Diagnostic Industry*, Aug. 2001.

Kothe, et al, "Characterization of a Modified, Stroma-Free Hemoglobin Solution as an Oxygen-Carrying Plasma Substitute," *Surgery, Gynecology & Obstetrics*, 161: 563-569 (1985).

Sehgal, et al., "Large-Volume Preparation of Pyridoxylated Hemoglobin with High P501.2," *Journal of Surgical Research*, 30: 14-19 (1981).

Savitsky, et al., "A Clinical Safety Trial of Stroma-Free Hemoglobin," *Clin. Pharmacol Ther.*, 73-80 (1978).

Issekutz, A., "Removal of Gram-Negative Enotoxin from Solutions by Affinity Chromatography," *Journal of Immunological Methods*, 61: 275-281 (1983).

Mok, W., "Cross-linked Hemoglobins as Potential Plasma Protein Extenders," *Federation Proceedings*, 34: 1458-1460 (1975).

*Intensive Care. Resuscitation. First Aid*, Malyshev, V.D., Ed., Moscow, "Meditsina", p. 142 (2000) (with translation).

(56) References Cited

OTHER PUBLICATIONS

*Clinical Surgery*, Condon, R., et al. Eds, pp. 204-208; pp. 433-434 (1998) (with translation).
Gould, S.A., et al., "The Life-Sustaining Capacity of Human Polymerized Hemoglobin when Red Cells Might Be Unavailable," *Journal of the American College of Surgeons*, 195(4): 445-455 (Oct. 2002).
Carson, J.L., et al., "Mortality and morbidity in patients with very low postoperative Hb levels who decline blood transfusion," *Transfusion*, 42: 812-818 (Jul. 2002).
Moore, F.A., et al., "Trauma Resuscitation," *ACS Surgery—Principles & Practice*, 31-61 (2002).
American College of Surgeons Committee on Trauma. Advanced Trauma Life Support Program for Physicians 1997 Instructional Manual, 6th, ed. Chicago: American College of Surgeons; 98-117 (1997).
Farlon, K.J., et al., "Changes in Red Cell Transfusion Practice among Adult Trauma Victims," *J. Trauma*, 44(4): 583-587 (1998).
Baker, J.B., et al., "Type and Crossmatch of the Trauma Patient," *J. Trauma*, 50(5): 878-881 (May 2001).
DeFoe, G.R., et al., "Lowest Hematocrit on Bypass and Adverse Outcomes Associated with Coronary Artery Bypass Grafting," *Ann Thorac Surg.*, 71: 769-776 (2001).
Wu, W.C., et al., "Blood Transfusion in Elderly Patients with Acute Myocardial Infarction," *New England Journal of Medicine*, 345(17): 1230-1236 (Oct. 2001).
"Practice Guidelines for Blood Component Therapy: A report by the American Society of Anesthesiologists Task Force on Blood Component Therapy," *Anesthesiology*, 84(3): 732-747 (Mar. 1996).
"Consensus Conference. Perioperative Red Blood Cell Transfusion," *JAMA*, 260(18): 2700-2703 (Nov. 1988).
Gould, S.A., et al., "Fluosol DA-20 As A Red Cell Substitute in Acute Anemia," *New England Journal of Medicine*, 314(26): 1653-1656 (Jun. 1986).
Spence, R.K., et al., "Fluosol DA-20 in the treatment of severe anemia: Randomized, controlled study of 46 patients," *Critical Care Medicine*, 18(11): 1227-1230 (Nov. 1990).
Spence, R.K., at al., "Is Hemoglobin Level Alone a Reliable Predictor of Outcome in the Severely Anemic Patient?" *The American Surgeon*, 58(2): 92-95 (1992).
Carson, J.L, at al., "Severity of Anaemia and Operative Mortality and Morbidity," *Lancet*, 1(8588): 727-729 (Apr. 1988).
Carson, J.L., at al., "Effect of anaemia and cardiovascular disease on surgical mortality and morbidity," *Lancet*, 348 (9034): 1055-1060 (Oct. 1996).
Viele, M.K., et al., "What can we learn about the need for transfusion from patients who refuse blood? The experience with Jehovah's Witnesses," *Transfusion*, 34(5): 396-401 (1994).
Sehgal L.R., at al., "Polymerized pyridoxylated hemoglobin: A red cell substitute with normal oxygen capacity," *Surgery*, 95: 433-438 (1984).
Amberson, W.R., et al., "Clinical Experience with Hemoglobin-Saline Solutions," *J. Applied Physiology*, 1(7): 469-489 (Jan. 1949).
Brandt, J.L., et al., "The Effects of Hemoglobin Solutions on Renal Functions in Man," *Blood*, 6: 1152-1158 (1951 ).
Miller, J.H., et al., "The Effect of Hemoglobin on Renal Function in The Human," *Journal of Clinical Investigation*, 30: 1033-1040 (Jul. 1951).
Savitsky, J.P., et al., "A clinical trial of stroma-free hemoglobin," *Clinical Pharmacology Journal*, 23(1): 73-80 (Jan. 1978).
Carmichael, F.J., et al., "A phase I study of oxidized raffinose cross-linked human hemoglobin," *Crit Care Med*, 28 (7): 2283-2292 (2000).
Kasper, S.M., et al., "Effects of a Hemoglobin-Based Oxygen Carrier (HBOC-201) on Hemodynamics and Oxygen Transport in Patients Undergoing Preoperative Hemodiulution for Elective Abdominal Aortic Surgery," *Anesth Analg*, 83: 921-927 (1996).
LaMuraglia, G.M., et al., "The reduction of the allogenic transfusion requirement in aortic surgery with a hemoglobin-based solution," *J. Vascular Surgery*, 31(2): 299-308 (Feb. 2000).
Sloan, E.P., et al., "Diaspirin Cross-Linked Hemoglobin (DCLHb) in the Treatment of Severe Traumatic Hemorrhagic Shock," *JAMA*, 282: 1857-1864 (Nov. 1999).
Gould, S.A., et al., "Clinical Utility of Human Polymerized Hemoglobin as a Blood Substitute after Acute Trauma and Urgent Surgery," *J. Trauma*, 43(2): 325-332 (Aug. 1997).
Gould, S.A., et al., "The First Randomized Trial of Human Polymerized Hemoglobin as a Blood Substitute in Acute Trauma and Emergent Surgery," *J Am Coli Surg*, 187(2): 113-122 (Aug. 1998).
Vengelen-Tyler, V., American Association of Blood Banks Technical Manual. 13th ed., Bethesda (MD): *American Association of Blood Banks*, p. 389-396 (1999).
Huston, P., et al., "Withholding Proven Treatment in Clinical Research," *New England Journal of Medicine*, 345 (12): 912-914 (Sep. 2001).
Emanuel, E.J., et al., "The Ethics of Placebo-Controlled Trials—A Middle Ground," *New England Journal of Medicine*, 345(12): 915-914 (Sep. 2001).
Carson, J.L, et al., "Mortality and morbidity in patients with very low blood counts who decline blood transfusion," *Transfusion*, 42: 812-818 (Jul. 2002).
Reiner, A.P., "Massive Transfusion," *Perioperative Transfusion Medicine*, p. 351-364 (1998).
Weiskopf, R.B., et al., "Human Cardiovascular and Metabolic Response to Acute, Severe Isovolemic anemia," *JAMA*, 279(3): 217-221 (Jan. 1998).
Wilkerson, D.K., et al., "Limits of cardiac compensation in anemic baboons," *Surgery*, 103(6): 665-670 (1988).
Levy, P.S., et al., "Oxygen Extraction Ratio: A Valid Indicator of Transfusion Need in a Limited Coronary Vascular Reserve?" *J. Trauma*, 32(6): 769-774 (Jun. 1992).
Standl, T., "Artificial oxygen carriers: Hemoglobin-based oxygen carriers—Current status 2004," *Transfusion Medicine and Hemotherapy*, 31(4): 262-268 (2004).
Toussaint, M., et al., "Effects of three Hb-based oxygen-carrying solutions on neutrophil activation in vitro: Quantitative measurement of the expression of adherence receptors," *Transfusion* (Bethesda), 41(2): 226-231 (Feb. 2001).
Yagi, K., "Simple Assay for the Level of Total Lipid Peroxides in Serum or Plasma," *Methods in Molecular Biology*, vol. 108. Free Radical and Antioxidant Protocols, D. Armstrong (Ed.) 1998. Humana Press Inc., Totowa, NJ.
Su Young Chae, et al., "Ioactive polymers for biohybrid artificial pancreas," *J. of Drug Targeting*, 9(6): 473-484 (2001).
Lacy & Kostanovsky, "Method for the Isolation of Intact Islets of Langerhans from the Rat Pancreas," *Diabetes*, 16: 35-39 (1967).
Avila, J.G., et al., "Improvement of Pancreatic Islet Isolation Outcomes Using Glutamine Perfusion During Isolation Procedure," *Cell Transplant*, 12: 877-881 (2003).
Zhou, et al., "Overexpression of Bcl-xL in B-cells prevents cell death but impairs mitochondrial signal of insulin secretion," *Am J Physiol Endocrinol Metab*, 278: E340-E351 (2000).
Oberholzer, J., et al., "Decomplementation with cobra venom factor prolongs survival of xenografted islets in a rat to mouse model," *Immunology*, 97: 173-180 (1999).
Ichii, et al., "A Novel Method for the Assessment of Cellular Composition and Beta-Cell Viability in Human Islet Preparations," *American Journal of Transplantation*, 5: 1635-1645 (2005).
Merriam-Webster Medline Plus definition of "suspension," http:--www.merriam-webster.com-medlineplus-suspension, assessed Jun. 15, 2015.
U.S. Appl. No. 11/626,727, Notice of Abandonment, dated Mar. 21, 2011.
U.S. Appl. No. 11/626,727, Non-Final Office Action, dated Sep. 7, 2010.
U.S. Appl. No. 11/626,727, Examiner Initiated Interview Summary, dated Aug. 31, 2010.
U.S. Appl. No. 11/626,727, Non-Final Office Action, dated Jan. 12, 2010.
International Search Report and Written Opinion, PCT/US2007/060989, "Polymerized Hemoglobin Media and Its Use in Isolation and Transplantation of Islet Cells," date of mailing Oct. 10, 2007.

(56) References Cited

OTHER PUBLICATIONS

International Preliminary Report on Patentability, PCT/US2007/060989, "Polymerized Hemoglobin Media and Its Use in Isolation and Transplantation of Islet Cells," date of mailing Aug. 7, 2008.
U.S. Appl. No. 13/041,685, Notice of Abandonment, dated Feb. 19, 2013.
U.S. Appl. No. 13/041,685, Non-Final Office Action, dated Aug. 3, 2012.
U.S. Appl. No. 13/016,758, Notice of Abandonment, dated Feb. 19, 2013.
U.S. Appl. No. 13/016,758, Non-Final Office Action, dated Aug. 3, 2012.
U.S. Appl. No. 13/706,758, Non-Final Office Action, dated Dec. 16, 2014.
U.S. Appl. No. 13/706,578, Non-Final Office Action, dated Nov. 16, 2015.
Wong, H. et al., "Identification and characterization of a protease by *Vibrio parahaemolyticus* in iron-limited medium," *Chinese Journal of Microbiology and Immunology* (Taipei), 27(4): 173-184 (Nov. 1994).

\* cited by examiner

A

B

A

B

A

B

METHOD OF ISOLATING CELLS FROM A TISSUE IN A MAMMAL

RELATED APPLICATIONS

This application is a continuation of U.S. application Ser. No. 13/041,685, filed Mar. 7, 2011, which is a continuation of U.S. application Ser. No. 11/626,727, now abandoned, filed Jan. 24, 2007, which claims the benefit of U.S. Provisional Application No. 60/761,663, filed Jan. 24, 2006. This application also is a continuation of U.S. application Ser. No. 13/016,758, filed Jan. 28, 2011, which is a divisional of U.S. application Ser. No. 12/161,542, now abandoned, filed Jul. 18, 2008, which is a U.S. National Stage Application of PCT/US07/60987, filed Jan. 24, 2007, which also claims the benefit of U.S. Provisional Application No. 60/761,663, filed Jan. 24, 2006.

The entire teachings of the above applications are incorporated herein by reference.

FIELD OF THE INVENTION

The application relates to the field of cell biology. In particular, the application relates to solutions, suspensions, methods, and processes useful for the isolation, culture, and transplantation of cells and tissues.

DESCRIPTION OF THE RELATED ART

The transplantation of cells, tissues, and organs holds great promise for the treatment of many diseases. For example, pancreatic islet transplantation can reverse insulin-dependent diabetes. Unfortunately, the procedure is hampered by a short supply of islets and a gradual loss of islet function after transplantation. The inconsistency of islet isolation outcomes has been a major limitation to widespread clinical application of islet transplantation. The following U.S. patents describe known methods of isolating, culturing, and/or transplanting pancreatic islets: U.S. Pat. Nos. 6,506,599, 6,562,620, 6,783,964, and 6,815,203.

Among the variety of factors influencing post-isolation islet yield, viability and function, ischemic time is of particular importance. The length of ischemia is inversely correlated with islet isolation outcomes. Ischemia renders cells more susceptible to oxidative stress by impairing mitochondrial antioxidant defenses. Providing $O_2$ to ischemic tissue has been shown to be a double edged sword due to reperfusion injury. Reactive Oxygen Species (ROS) produced by mitochondria play a significant role in this type of injury. Oxidative stress to pancreatic islets during the isolation procedure has been well documented, and the use of antioxidants has been shown to protect islets from oxidative injury. Organ preservation solutions such as histidine-tryptophan-ketoglutarate (HTK) and University of Wisconsin (UW) solution are designed to protect pancreatic tissue from the deleterious effects of ischemia, but do not prevent ischemia per se.

Maintaining an appropriate $O_2$ level would seem important to prevent ischemic damage and reperfusion injury during organ preservation, pancreatic islet isolation, and cell culture. Indeed, artificial oxygen carriers, such as perfluorocarbons (PFC), have a beneficial effect on islet isolation and transplantation outcomes when used during pancreas preservation with UW solution in the two layer method (TLM). Artificial oxygen carriers are synthetic solutions capable of binding, transporting and unloading $O_2$. Artificial oxygen carriers have been originally developed as blood substitutes, but none of the PFC based products have been approved for clinical use, and in clinical trials anaphylactic reactions were observed. Moreover, PFCs have the inconvenience of being hydrophobic and difficult to keep in aqueous solution.

Hemoglobin-based $O_2$ carriers (HBOC's), such as PolyHeme, are water soluble. U.S. Pat. No. 6,498,141, which is hereby incorporated by reference in its entirety, describes the preparation of representative HBOC's. In contrast to PFC, PolySFH-P polymerized hemoglobin gives an $O_2$ saturation curve similar to that of red blood cells. No anaphylactic reactions have been observed in phase I and II trials of PolyHeme. PolySFH-P, which is described below, is another example of an HBOC. Both PolySFH-P polymerized hemoglobin and PolySFH-P are essentially tetramer-free, substantially stroma-free, polymerized, pyridoxylated hemoglobin derived from human blood.

There is a need for HBOC-containing solutions and suspensions useful in the isolation, culture, and transplantation of cells, tissues, and organs. This patent application describes such solutions and suspensions, as well as process for making and methods of using them.

SUMMARY

This invention provides solutions containing hemoglobin-based $O_2$ carriers (HBOC's), methods for making these solutions and methods for using such solutions for isolating cells, tissues and components of tissues from an animal, most preferably a human. The invention specifically provides solutions and suspensions for use in isolating, culturing, and transplanting cells, tissues, and organs.

In one aspect, a solution of the invention comprises (a) polymerized hemoglobin derived from a mammal and (b) one or more enzymes. In a particular aspect, the polymerized hemoglobin is derived from human blood and the enzyme is a protease, such as collagenase. In another aspect, the solution further comprises cell culture medium, such as RPMI or CMRL or similar commercially available or proprietary culture media.

In a second aspect, a solution of the invention comprises (a) polymerized hemoglobin derived from a mammal and (b) cell culture medium.

In further aspects, the solutions of the invention comprise polymerized and pyridoxylated hemoglobin derived from human blood. Further, the solutions may be oxygenated.

In a third aspect, the invention provides suspensions comprising (a) polymerized hemoglobin derived from mammalian blood and either (b1) mammalian hematopoietic cells or (b2) mammalian pancreatic tissue or mammalian islet cells. In particular aspects, the suspensions may further comprise cell culture medium, such as RPMI or CMRL or similar commercially available or proprietary culture media, and/or an enzyme, including proteases, e.g., collagenases.

Moreover, the invention provides numerous methods of using the solutions and suspensions of the invention. For example, the invention provides a method of isolating mammalian cells, such as pancreatic islet cells, comprising contacting the cells with a solution of the invention. The invention also provides a method of treating a mammal with diabetes, comprising the step of transplanting to the mammal an effective amount of pancreatic islets isolated according to the methods of the invention. Moreover, the invention provides methods of preserving mammalian tissue, of aiding the recovery of mammalian cells following their isolation, of maintaining mammalian cells, and of propagating mammalian cells, all comprising contacting the mammalian cells or tissue with a solution of the invention. In such methods, it is preferable for the cells or tissue to remain viable following their contact with a solution of the invention.

Also, the invention provides methods of maintaining viability in mammalian cells, tissues, and/or organs during donor management, organ procurement and transportation and storage and transplant of the mammalian cells, tissues, and/or organs, the method comprising contacting the cells, tissues, and/or organs with a solution of the invention. Such methods include, for example, methods of perfusing organs with a solution of the invention prior to harvesting of those organs for transplantation. In a particular aspect, the invention provides methods of preserving a whole mammalian organ, comprising contacting the whole organ with a solution comprising (a) polymerized hemoglobin derived from mammalian blood and (b) cell culture medium.

Furthermore, the invention provides processes of preparing the foregoing solutions and suspensions.

Specific preferred embodiments of the invention will become evident from the following more detailed description of certain preferred embodiments and the claims.

DETAILED DESCRIPTION

Figure 1:
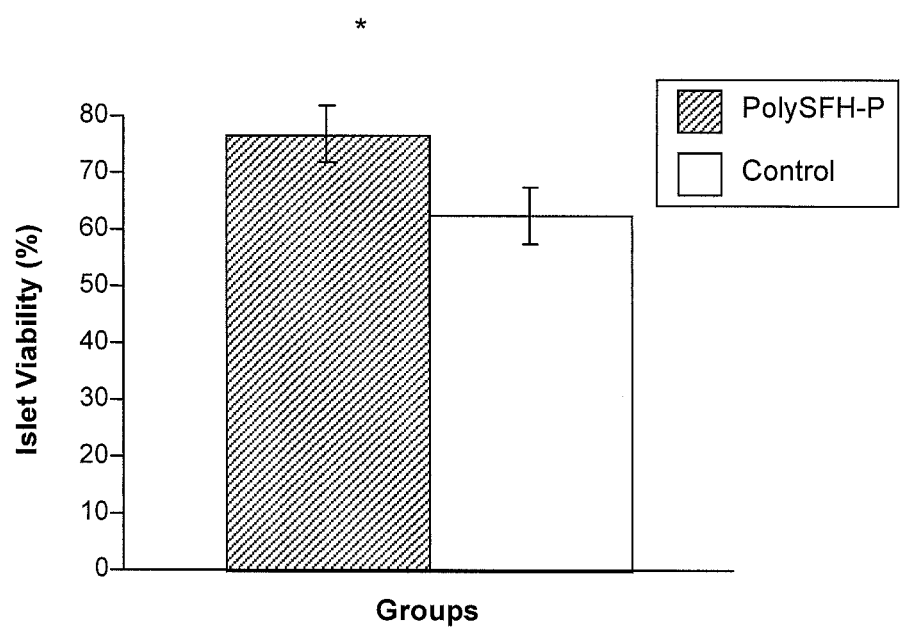
FIG. 1 shows the viability of islets from both groups expressed in percentages 24 hours after isolation, represented as means±SEM. PolySFH-P isolations (n=9) Control isolations (n=9) for each group. *p=0.047.
Figure 2:
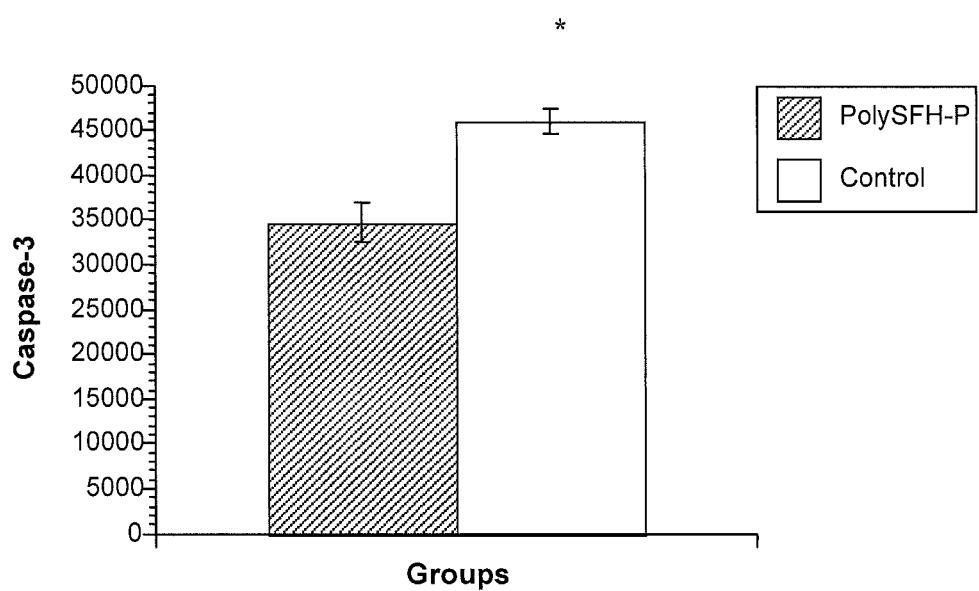
FIG. 2 shows caspase-3 levels measured in islets from PolySFH-P and control groups 24 hrs after isolation as a marker for apoptosis, n=3 isolations per group. Caspase-3 levels are significantly lower in the PolySFH-P group than in the control. *p=0.011.
Figure 3:
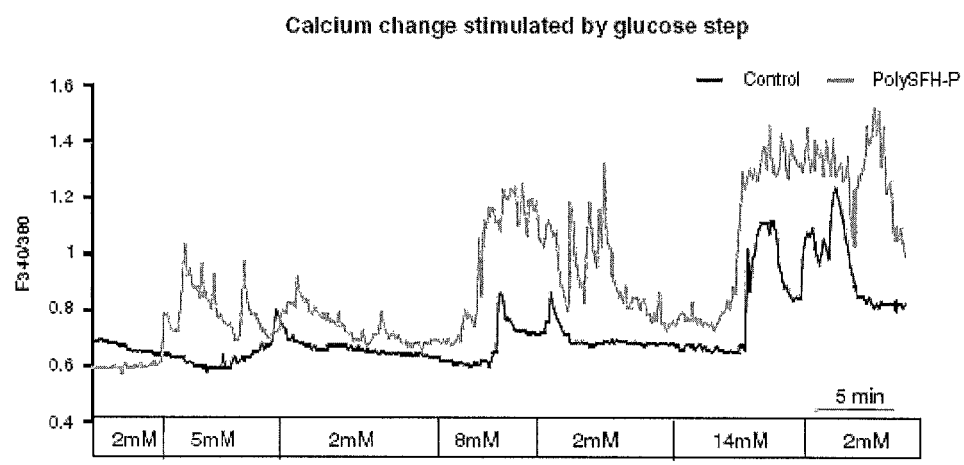
FIG. 3A shows changes in ratio-metric values (Fura 2/AM) as a measurement of intracellular calcium levels in two representative islets under basal (2 mM) and stimulated (5, 8, or 14 mM) glucose conditions.
FIG. 3B shows the percentage of intracellular calcium change in response to glucose stimulation (5, 8 or 14 mM glucose concentrations) in islets from PolySFH-P and control groups, (n=25 islets per group), mean±SEM. *p<0.05.
Figure 3:
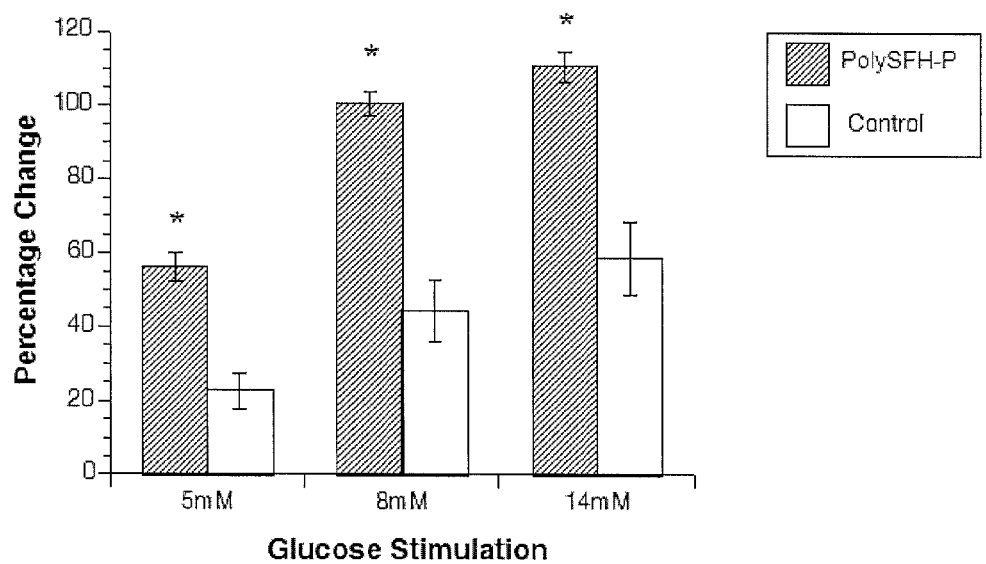

This invention provides solutions comprising polymerized hemoglobin derived from blood, most preferably human blood, and an enzyme, most preferably a proteolytic enzyme. The invention further provides methods for preparing said solutions, and methods for using said solutions for isolating cells, tissue and components of tissues, most preferably pancreatic islets, from animal organs and tissues, most preferably human organs and tissues. The invention also provides suspensions of said cells, tissues and components of tissues, preferably suspensions of pancreatic islets and most preferably human pancreatic islets.

The invention further provides methods of preserving whole mammalian organs that have been removed from a mammal's body, for example for transplantation into another mammal of the same or different species. These methods comprise contacting the whole organ with a solution comprising (a) polymerized hemoglobin derived from mammalian blood and (b) cell culture medium. The invention may be used to preserve any mammalian organ; ovine, human, and non-human primate organs are preferred. Examples of organs that may be preserved using the solution of polymerized hemoglobin and cell culture medium are lung, kidney, liver, and heart. The organ may alternatively be skin, for example facial skin being transplanted from an accident victim to a patient. Preferably, the solution and whole organ is maintained at a temperature of from about 0° C. to about 4° C. prior to transplantation.

In one embodiment, the solutions, suspensions, methods, and processes that are the subject of this patent application comprise or involve polymerized hemoglobin. Preferably, the polymerized hemoglobin is derived from human blood. For use in preserving organs for transplantation, the preferred hemoglobin will match the organ donor species, which will typically be human or other primate organs.

As used herein, the term "hemoglobin" refers to hemoglobin from mammals (preferably bovine, ovine, or human hemoglobin, more preferably human hemoglobin), synthetic hemoglobin, hemoglobin obtained by transgenic means, hemoglobin obtained from cell lines that naturally produce or have been manipulated to produce hemoglobin in vitro, hemoglobins obtained in mutant form, and chemically modified forms of hemoglobin. The hemoglobin of the invention comprises hemoglobin species including but not limited to Hemoglobin A, ($\alpha_2\beta_2$), Hemoglobin A2, ($\alpha_2\beta_2$) and fetal hemoglobin ($\alpha_2\gamma_2$), as well as mixtures thereof.

As used herein, the phrase "polymerized hemoglobin" refers to hemoglobin that has been polymerized so that it can serve as a physiologically competent oxygen carrier, wherein the placement of molecular bridges between molecules or tetrameric subunits of the hemoglobin results in the increased size and weight of the resulting polymerized molecule with respect to native or tetrameric hemoglobin. For example, polymerized hemoglobin can absorb oxygen at the partial pressures of oxygen prevailing at the site of oxygenation of hemoglobin, for example, in the lungs of humans, and release the bound oxygen to the tissues of the same organisms in amounts that are life supporting. Polymerized hemoglobins can be obtained, for example, by treatment with glutaraldehyde or raffinose, as discussed in U.S. Pat. No. 5,998,361, which is hereby incorporated by reference. Polymerized hemoglobins are also described, for example, in U.S. Pat. No. 6,498,141, which is hereby incorporated by reference.

The polymerized hemoglobin derived from human blood mayor may not be pyridoxylated, as described in U.S. Pat. No. 6,498,141. Pyridoxylation may be used to modulate the p50 of the polymerized hemoglobin to a desirable range. Thus, for example, when using hemoglobin derived from human blood and the p50 of the solution containing the polymerized hemoglobin is desired to be within the range of normal human blood, the hemoglobin is preferably pyridoxylated, as described in U.S. Pat. No. 6,498,141.

In certain embodiments, the polymerized hemoglobin can be PolySFH-P, which is an example of polymerized hemoglobin derived from human blood. PolySFH-P is essentially tetramer-free, substantially stroma-free, polymerized, pyridoxylated hemoglobin derived from human blood. In certain embodiments, the solutions disclosed herein comprise polymerized hemoglobin derived from human blood and at least one of the following: a buffer, cell culture medium, or an enzyme (such as a protease). The solutions disclosed herein may contain one, two, or three of these—in addition to polymerized hemoglobin derived from human blood. A solution of the invention can also comprise a reducing agent, such as ascorbic acid, to serve as a hemoglobin preservative. Furthermore, the solutions may or may not be oxygenated.

"Buffer," as used herein, refers to a system, such as a solution, that acts to minimize the change in concentration of a specific chemical species in solution against addition or depletion of the species, particularly with regard to the hydrogen ion concentration (pH) of the solution. Examples of buffers are well-known to those of skill in the art.

"Cell culture medium," as used herein, refers to a medium suitable for the culture, maintenance, proliferation, and/or growth of cells in vitro. Examples of cell culture media that can be used in a solution of the invention are disclosed in U.S. Pat. Nos. 6,670,180 and 6,730,315, which are incorporated by reference. One of skill in the art will recognize that the type of cell culture media useful in a solution of the invention can be selected based on the type of cell, tissue, and or organ for which the solution is to be used. For example, where the cells are pancreatic islets, the cell culture medium can be RPMI, as described herein. Alternative cell culture media, including Eagles Minimal Media, Dulbecco's Modified Eagle's Media, and others known to those with skill in the art, are commercially available (for example, from GIBCO, Long Island, N.Y. and Sigma Chemical Co., St; Louis. Mo.) and fall within the scope of components of the invention set forth herein.

"Protease" (or "proteolytic enzyme"), as used herein, refers to an enzyme that catalyzes the splitting of peptide bonds in a protein. Collagenase is an example of a protease. Other examples of proteases are well-known to those of skill in the art, including but not limited to trypsin, chymotrypsin, pepsin, furin, dispace, thermolysin, elastase, and mixtures thereof such as pancreatin and liberase (a purified enzyme blend of collagenase isoforms I and II from *Clostridium histoliticum* and thermolysin from *Bacillus thermoproteolyticus*).

"Enzymatically produced," as used herein, refers to the action of an enzyme provided in combination with polymerized hemoglobin according to the invention, particularly proteolytic enzymes useful in digesting extracellular matrix proteins and other proteins involved in maintaining the integrity of a tissue or organ in vivo.

The suspensions disclosed herein comprise polymerized hemoglobin derived from mammalian, preferably, human, blood and either (b1) mammalian hematopoietic cells or (b2) mammalian pancreatic tissue or mammalian pancreatic islets. The suspensions may further comprise cell culture medium and/or enzymes (such as a protease). Moreover, the suspensions may or may not be oxygenated. By "hematopoietic cells" is meant cells found within mammalian blood, including white blood cells (e.g., monocytes and lymphocytes), platelets, and red blood cells (erythrocytes).

In certain embodiments, the solutions and/or suspensions of the invention can be used in various methods for maintaining the viability of cells, tissues, and/or organs under various conditions. For example, they can be employed in methods of isolating mammalian cells, such as pancreatic islets. In addition, they can be used in methods of preserving mammalian tissue; of aiding the recovery of mammalian cells following their isolation; of maintaining cells in cell culture conditions; and of propagating cells. Moreover, they can be used in methods of treating a mammal with diabetes, comprising contacting pancreatic islets with the solutions and/or suspensions of the invention. For example, pancreatic islets can be isolated from a donor patient using a solution of the invention and transplanted into a recipient patient. As another example, a solution of the invention can be used for maintaining viability of cells, tissues, and/or organs in a body (such as in a cadaver) and outside a body (such as during transport or transplantation surgery). Additionally, a solution of the invention can be used to improve organ transplantation success, by perfusion of the organ with a solution of the invention prior to harvesting the organ.

Preferred solutions containing polymerized hemoglobin are aqueous and are formulated to contain from about 5-15 g/dL of polymerized hemoglobin, more preferably from about 8-12 g/dL of polymerized hemoglobin, and most preferably from about 9-11 g/dL of polymerized hemoglobin. Particularly preferred solutions contain about 10 g/dL of polymerized hemoglobin.

Preferred solutions containing polymerized hemoglobin are formulated to have a pH of from about 7-8, more preferably from about 7.5-7.9, most preferably from about 7.3-7.6.

Preferred solutions containing polymerized hemoglobin and cell culture medium contain the above amounts of hemoglobin and from about 0.5× to 2× cell culture medium (where IX medium is a concentration equivalent to 1×RPMI). More preferred polymerized hemoglobin/cell culture medium solutions contain about 1× cell culture medium.

Solutions of polymerized hemoglobin and an enzyme, preferably a protease such as, for example, collagenase or liberase, are formulated to contain the above amounts of hemoglobin and from about 0.1-10 mg/mL of the enzyme. Preferred solutions are formulated to contain from about 0.5-5 mg/mL of enzyme, more preferably from about 0.75-1.25 mg/mL of enzyme. Particularly preferred solutions contain about 1 mg/mL of enzyme.

Solutions of polymerized hemoglobin, cell culture medium, and enzyme are formulated to contain the amounts of these components described above and within the above-recited pH ranges.

Processes for preparing the solutions and suspensions of the invention are also disclosed herein. Generally, the solutions and suspensions can be prepared by mixing the components thereof. Oxygenating the solutions and suspensions can be achieved, for example, by bubbling 100% $O_2$ gas through the solutions and suspensions for a sufficient period of time, or by otherwise contacting the solutions and suspensions with $O_2$ gas.

The Examples which follow are illustrative of specific embodiments of the invention, and various uses thereof. They set forth for explanatory purposes only, and are not to be taken as limiting the invention.

EXAMPLE 1

Preparation of Polymerized Hemoglobin Solution

In vitro culture media containing collagenase and with or without the addition of PolySFH-P polymerized hemoglobin were prepared as follows. A solution containing 10 g/dL PolySFH-P formulated with RPMI 1640 cell culture medium ("PolySFH-P/RPMI solution") was prepared by Northfield Industries (Evanston, Ill.) for islet isolation. PolySFH-P/RPMI solution was prepared by modifying the procedure described in Example 1 of U.S. Pat. No. 6,498,141. More specifically, Example 1 of U.S. Pat. No. 6,498,141 was followed from the beginning through the step at Tank 8. Starting at Tank 9, the procedure was as follows. Polymerized hemoglobin derived from human blood (PolySFH-P) was concentrated to about 7 g/dL and the pH of the solution was adjusted to between 7.30 and 7.60 with 0.1 M HCl. This solution was concentrated to 12 g/dL PolySFH-P. A sufficient amount of 10×RPMI solution containing 2.5 g/L ascorbic acid and water for injection ("WFI") was added to produce a final PolySFH-P/RPMI solution containing 10 g/dL PolySFHP, 1×RPMI, and 0.25 g/L ascorbic acid. The pH of the PolySFH-P/RPMI solution was verified to be between 7.30 and 7.60. PolySFH-P/RPMI solution was then sterile filtered and 250 mL were transferred aseptically into 500 mL bags. Bags were filled only half-full to allow for simplified oxygenation of the solution (within the bag) at the time of use. Filled bags were stored at 2-8° C.

10×RPMI solution containing 2.5 g/L ascorbic acid was prepared as follows. RPMI 1640 powder without $NaHCO_3$, phenol red and L-Glutamine, obtained from Cellgro (Mediatech, Herndon, Va.), was added to water for injection to obtain a concentration 10 times as concentrated as 1×RPMI 1640 (see below). 7.5% $NaHCO_3$, obtained from Invitrogen (Carlsbad, Calif.), was added to obtain a concentration of 267 mL/L. 200 mM L-Glutamine, received as a frozen solution from Invitrogen, was thawed and added to obtain a concentration of 102.5 mL/L. In addition, ascorbic acid was added to obtain a final concentration of 2.5 g/L.

EXAMPLE 2

2A. Experiments were conducted to determine the rate of oxygenation and conversion of PolySFH-P polymerized hemoglobin to methemoglobin during oxygenation and holding at 37° C. As a control, 100 mL samples of PolySFH-P polymerized hemoglobin are oxygenated utilizing compressed air (21% $O_2$) or compressed oxygen (99.4% $O_2$) to not less than 85% oxyhemoglobin ($O_2Hb$). The percent oxygen saturation can be measured by cooximetry such as that employed by Instrumentation Laboratories IL-482 or IL-682. The PolySFH-P polymerized hemoglobin samples are then heated to 37° C. and held at this temperature for not less than 20 minutes. After the 20-minute hold period, samples are tested utilizing cooximetry to determine the amount of methemoglobin (MetHb) conversion.

Cooximetry Results:

I A—Oxygenation of PolySFH-P polymerized hemoglobin (using compressed air/21% $O_2$, 8 standard cubic feet/hour)

| Sample | Total Hb (g/dL) | % $O_2Hb$ | % COHb | % Met Hb | Reduced Hb % |
|---|---|---|---|---|---|
| End of Oxygenation | 10.1 | 85.7 | 2.4 | 3.3 | 8.6 |
| End of 20 minute hold | 10.5 | 59.6 | 4.2 | 17.6 | 18.6 |

I B—Oxygenation of PolySFH-P polymerized hemoglobin (using compressed gas/99.4% $O_2$)

| Sample | Total Hb (g/dL) | % $O_2Hb$ | % COHb | % Met Hb | Reduced Hb % |
|---|---|---|---|---|---|
| End of Oxygenation | 10.5 | 90.6 | 2.4 | 2.1 | 4.9 |
| End of 20 minute hold | 10.2 | 79.7 | 3.3 | 9.3 | 7.8 |

Approximately 45 min. were required to oxygenate 100 mL PolySFH-P polymerized hemoglobin (using compressed air comprising about 21% $O_2$) to not less than 85% $O_2Hb$; alternatively, 100 mL PolySFH-P could be oxygenated to not less than 85% $O_2Hb$ in approximately 15 minutes using compressed oxygen (99.4% $O_2$). The results shown above established that the process of oxygenating PolySFH-P polymerized hemoglobin did not lead to significant conversion of hemoglobin to the Met Hb form. However, the method used for oxygenation did affect the percent Met Hb formed once PolySFH-P polymerized hemoglobin was heated to 37° C. The first method, using compressed air, led to a higher conversion to Met Hb (17.6% Met Hb) as compared to using compressed oxygen (9.3% Met Hb). The amount of MetHb formed was directly proportional to the amount of time taken to oxygenate PolySFH-P polymerized hemoglobin or the time kept at 37° C., or both. Despite this conversion of a small amount of the oxygenated PolySFH-P polymerized hemoglobin to the Met Hb form, a significant amount of Hb (79.7%) remained that was capable of carrying oxygen to the islet cells.

2B. Experiments were also conducted to determine if collagenase or liberase interfered with PolySFH-P polymerized hemoglobin or caused product degradation.

For these experiments, initial samples were taken and analyzed by Cooximetry and HPLC (Size Exclusion) as reference samples. A 100 mL sample of PolySFH-P polymerized hemoglobin at 4-8° C. was oxygenated to not less than 85.0% $O_2$ Hb. Cooximetry samples were then taken at approximately 15-minute intervals during oxygenation to determine a time course of the extent of oxygenation. Once the oxyhemoglobin level was not less than 85.0% O₂Hb, Cooximetry and HPLC samples were analyzed to determine impact to the product and MetHb levels. Once PolySFH-P polymerized hemoglobin has been oxygenated, one of the enzymes to be tested (collagenase or liberase) was added to PolySFH-P polymerized hemoglobin (1 mg/1 mL) at 4-8° C. and kept at this temperature for 10 minutes. After the 10-minute at 4-8° C., Cooximetry and HPLC samples were evaluated for PolySFH-P polymerized hemoglobin degradation and methemoglobin conversion. The PolySFH-P polymerized hemoglobin/enzyme solution was heated to 37-39° and this temperature maintained for approximately 20 minutes. Cooximetry and HPLC samples were then tested for PolySFH-P polymerized hemoglobin degradation and methemoglobin conversion. HPLC analysis was used to determine degradation of the PolySFH-P polymers by analyzing for differences over time in the integrated areas of the peaks representing each polymeric species.

II A—Oxygenation of PolySFH-P Polymerized Hemoglobin

| Sample | Total Hb | % O₂Hb | % COHb | % Met Hb | Reduced Hb % |
|---|---|---|---|---|---|
| Initial (time (t) 0) | 9.8 | 5.5 | 7.0 | 2.5 | 85.1 |
| 1ˢᵗ sample (t o + 22 minutes) | 9.9 | 46.1 | 5.2 | 2.8 | 45.9 |
| 2ⁿᵈ sample (t 0 + 40 minutes) | 10.0 | 75.4 | 3.6 | 2.5 | 18.5 |
| 3ʳᵈ sample (t 0 + 55 minutes | 10.3 | 88.3 | 2.3 | 2.9 | 6.5 |

II A—PolySFH-P Polymerized Hemoglobin+Collagenase Enzyme

| Sample | Total Hb | % O₂Hb | % COHb | % Met Hb | Reduced Hb % |
|---|---|---|---|---|---|
| PolySFH-P polymerized hemoglobin + collagenase cold | 10.3 | 87.3 | 2.4 | 3.5 | 6.8 |
| PolySFH-P polymerized hemoglobin + collagenase at 37° C. | 10.5 | 45.9 | 4.6 | 21.4 | 28.2 |

II A—Integrated Area % by HPLC During Oxygenation and Collagenase Addition

| Sample | 256 Peak | 192 Peak | 128 Peak | Tetramer Peak |
|---|---|---|---|---|
| Poly 70 Standard | 58.7684 | 22.9897 | 17.6471 | 0.5947 |
| Initial Sample | 59.3603 | 22.1871 | 17.5184 | 0.9341 |
| End of Oxygenation | 59.1316 | 22.2671 | 17.6236 | 0.9777 |
| PolySFH-P polymerized hemoglobin + collagenase cold | 58.8743 | 22.5339 | 17.6612 | 0.9306 |
| PolySFH-P polymerized hemoglobin + collagenase at 37° C. | 58.3968 | 22.6292 | 18.1017 | 0.8723 |

II B—Oxygenation of PolySFH-P Polymerized Hemoglobin

| Sample | Total Hb | % O₂Hb | % COHb | % Met Hb | Reduced Hb % |
|---|---|---|---|---|---|
| Initial (time (t) 0) | 9.8 | 5.5 | 7.0 | 2.5 | 85.1 |
| 1ˢᵗ sample (t 0 + 20 minutes) | 10.3 | 47.9 | 5.2 | 3.0 | 43.9 |
| 2ⁿᵈ sample (t 0 + 44 minutes) | 10.0 | 86.4 | 2.9 | 2.4 | 8.3 |

II B—PolySFH-P Polymerized Hemoglobin+Liberase Enzyme

| Sample | Total Hb | % O₂Hb | % COHb | Met Hb | Reduced Hb % |
|---|---|---|---|---|---|
| PolySFH-P polymerized hemoglobin + liberase cold | 10.2 | 88.5 | 2.7 | 2.3 | 6.5 |
| PolySFH-P polymerized hemoglobin + liberase at 37° C. | 10.8 | 45.6 | 4.7 | 26.6 | 23.2 |

II B—Integrated Area % by HPLC During Oxygenation and Liberase Addition

| Sample | 256 Peak | 192 Peak | 128 Peak | Tetramer Peak |
|---|---|---|---|---|
| Poly 70 Standard | 59.2357 | 22.9497 | 17.2487 | 0.5659 |
| Initial Sample | 59.3603 | 22.1871 | 17.5184 | 0.9341 |
| End of Oxygenation | 59.4932 | 22.0803 | 17.4739 | 0.9526 |
| PolySFH-P polymerized hemoglobin + Liberase cold | 58.9218 | 22.3305 | 17.7972 | 0.9505 |
| PolySFH-P polymerized hemoglobin + Liberase at 37° C. | 57.2619 | 22.9087 | 18.8117 | 1.0176 |

These consistent integrated areas for each peak demonstrated that collagenase and liberase did not interfere with PolySFH-P polymerized hemoglobin or cause product degradation as evaluated by HPLC analysis.

2C. Experiments were further conducted to establish the effect of RPMI on PolySFH-P polymerized hemoglobin to evaluate the suitability of PolySFH-P polymerized hemoglobin-supplemented RPMI for use in pancreatic islet cell harvesting.

For the experimental study of PolySFH-P polymerized hemoglobin with RPMI 1640, a 100 mL sample of PolySFH-P polymerized hemoglobin at 4-8° C. was oxygenated to not less than 85.0% O₂Hb. A Cooximetry sample was evaluated for the extent of oxygenation. Once the oxyhemoglobin level was not less than 85.0%, an osmolality sample was evaluated as a control. The RPMI 1640 was then added to PolySFH-P polymerized hemoglobin (1 g/100 mL) at 4-8° C. and thoroughly mixed to homogeneity prior to determining the osmolality of the mixture.

Because these procedures produced a hyperosmotic solution, a buffer solution of RPMI (10.10 g/1.0 L) was formulated. The buffer solution was used to carry out a fourvolume wash (diafiltration) of the 200 mL PolySFH-P polymerized hemoglobin. Upon completion of the diafiltration, the Cooximetry and osmolality of the sample was tested.

III A—Osmolality Results During Oxygenation and RPMI Addition

| Sample | Osmo (mmol/kg) |
|---|---|
| PolySFH-P polymerized hemoglobin control | 343 |
| PolySFH-P polymerized hemoglobin with RPMI | 600 |

III B—Osmolality Results of RPMI Diafiltration

| Sample | Osmo (mmol/kg) |
|---|---|
| PolySFH-P polymerized hemoglobin control | 331 |
| PolySFH-P polymerized hemoglobin during recirculation | 259 |
| PolySFH-P polymerized hemoglobin Post RPMI Diafiltration | 268 |
| RPMI Buffer | 257 |

Addition of RPMI to PolySFH-P polymerized hemoglobin resulted in an osmolality of 600 mmol/kg. PolySFH-P polymerized hemoglobin used with RPMI media in this fashion resulted in a hyperosmotic solution which had the potential to negatively impact islet cells. Consequently, this solution would be inappropriate for islet cell harvesting. However, when the RPMI was formulated into a buffer solution with ascorbic acid and used for diafiltration, the resulting solution of PolySFH-P polymerized hemoglobin+ RPMI had an osmolality of 268 mmol/kg. With a slight adjustment to the osmolality of the solution, this mixture would be acceptable for use in islet cell harvesting.

EXAMPLE 3

Islet Isolation

Pancreatic islets were isolated from experimental animals (rats) using in vitro culture media containing collagenase and with or without the addition of PolySFH-P prepared as described in Example 1. All animal procedures involving animals were performed in accordance with the guidelines of the National Institutes of Health and the Animal Care Committee (ACC) at the University of Illinois Chicago. Male Lewis rats (Harlan Industries, Indianapolis, Ind.), weighing between 175-200 g were used as pancreas donors for islets. Animals were anesthetized by isoflurane inhalation using a vaporizer and masks (Viking Medical, Medford Lakes, N.J.). There were 2 experimental groups: PolySFH-P Group (PolySFH-P/RPMI solution containing collagenase, n=40 rats) and Control Group (RPMI 1640 medium containing collagenase, n=40 rats).

Rat islet isolation was performed following a conventional technique previously described in Lacy & Kostanovsky (1967, *Diabetes* 16:35-39), modified by using the warm ischemia model described in Avila et al. (2003, *Cell Transplant* 12:877-881). Briefly, after the animal was anesthetized, a laparotomy incision was performed followed by incision into the thoracic cavity and section of the heart for euthanasia by exsanguination. The abdominal cavity was closed, covered with gauze and left for 30 minutes before pancreas perfusion.

Collagenase type XI (Sigma Chemical Co., St. Louis, Mo.) was reconstituted to a final concentration of 1 mg/mL in either PolySFH-P/RPMI solution (Treatment) or RPMI 1640 medium (Control), and both Treatment and Control were oxygenated by bubbling the solutions with 100% $O_2$ for 15 minutes. The effect of collagenase on the stability of polymerized hemoglobin was determined by HPLC analysis. PolySFH-P/RPMI solution was incubated with or without collagenase under different conditions, before and after oxygenation, at 4 and 37° C. HPLC analysis did not reveal any degradation of PolySFH-P. In addition, the formation of Methemoglobin (MetHb) and carboxyhemoglobin (COHb) was analyzed after various oxygenation times. No significant MetHb or COHb formation was found.

The oxygenated enzyme solutions were injected via the bile duct and into the main pancreatic duct for distention of the pancreas. The pancreas was then excised, and each pancreas placed in a 50 mL conical tube with 7.5 mL of its respective perfusion solution. This was followed by incubation in a 37° C. water bath (digestion phase) for 18 minutes. After this step, each pancreas was gently shaken in the tubes, washed with cold RPMI 1640 medium, and transferred into a 500 mL beaker. Islets were purified from the exocrine tissue by discontinuous Ficoll density gradients (Mediatech Inc., Herndon, Va.). In this procedure, the islet/exocrine tissue mixtures were applied to the Ficoll density gradients and then centrifuged for 15 minutes at 1,500 rpm; the islet cell portion of the gradient was identified by visual inspection from the middle layer of the Ficoll gradient and handpicked. Isolated islets were then washed and cultured in RPMI 1640 medium containing 10% fetal calf serum (FBS), 10% Penicillin/Streptomycin (Invitrogen) and without glutamine, for 24 hours culture 5 at 37° C.

$O_2$ tension and pH were measured in the pancreas perfusion medium (PolySFH-P and Control) before and after digestion using a blood gas analyzer (ABL/700 Radiometer, Copenhagen, Denmark). $O_2$ tension was higher in PolySFH-P compared to the Control in the perfusion solution (containing distended pancreata) before the digestion phase (Table III). Moreover, PolySFH-P maintained the pH in physiological range, whereas in the Control group the pH fell significantly during the digestion phase (Table III). These results were not the result of differences in the buffering capacities of the treatment and control solutions, which were determined to be similar (data not shown).

TABLE III

| | $O_2$ Tension (mmHg) Pre-digestion | $O_2$ Tension (mmHg) Post-digestion | pH Initial (without O2) | pH Initial (with O2) | pH Pre-digestion | pH Post-digestion |
|---|---|---|---|---|---|---|
| PolySFH-P | 381.7 ± 35.3* | 184.3 ± 39.8 | 7.4 ± 0.04** | 7.4 ± 0.03† | 7.4 ± 0.03†† | 7.2 ± 0.06*** |
| Control | 202.3 ± 28.2 | 128.3 ± 27.8 | 7.1 ± 0.03 | 7.8 ± 0.01 | 6.9 ± 0.04 | 6.6 ± 0.11 |

In Table III, oxymetry values ($O_2$ and pH) are shown for perfusion media (PolySFH-P/RPMI solution ("PolySFH-P") and RPMI 1640 medium ("Control")) before and after digestion.
Values are means ± SEM, n = 12 rats per group.
*p = 0.01;
**p = 0.009;
†p = 0.006;
††p = 0.001;
***p = 0.009.

EXAMPLE 4

In Vitro Assessment of Islet Yield, Viability, and Function

The results of islet isolation using a collagenase IX/RPMI 1640 solution with or without Poly-SFH-P as described in Example 3 were analyzed for yield, viability and islet cell function. To determine islet yield, dithizone stained islets from a representative sample were counted under a stereoscopic microscope (Leica Microsystems, Bannockburn, Ill.). Islet viability was assessed by staining with trypan blue dye (Sigma). Islets stained more than 25% of its surface were considered dead. Live versus dead islets were assessed in a representative sample, where a minimum of 50 islets were counted per sample.

Cell death was further characterized as follows. The level of apoptotic cell death was measured using a living cell fluorescein active caspase-3 staining kit (Biovision, Mountain View, Calif.). In these assays, an aliquot of 1,200 islets per group was counted and divided into four Eppendorf tubes with 300 μL of media (RPMI 1640 supplemented with 10% FBS and 10% Pen/Strep). A fluorescent dye for Caspase-3 (FITC-DEVD-FMK; 1 μL per tube) was added into two of the tubes of each group and the other two tubes were left untreated as a control. The tubes were incubated for 1 hour at 37° C. under a 5% $CO_2$ atmosphere. Cells were pelleted from the suspension by centrifugation at 1,100 rpm for 1 min and supernatant removed. The pelleted cells were then resuspended using the wash buffer in the kit according to the manufacturer's instructions and washed twice in this buffer by centrifugation and resuspension. The cells were then resuspended in 100 μL of the wash buffer and the contents of each tube transferred into individual wells of a black microtiter plate. Fluorescence intensity was measured using an excitation wavelength of 485 nm and emission wavelength of 535 nm in a fluorescent plate reader (GENios, Tecan US Inc., Durham, N.C.).

Islet cell function was assayed by incubation with varying amounts (5, 8 and 12 mM) glucose. Intracellular divalent calcium ion concentration during glucose stimulation was measured for functional evaluation in isolated islets, using standard wide-field fluorescence imaging with dual-wavelength excitation fluorescent microscopy. In these assays, islets were loaded with a calcium-specific dye (Fura-2/AM; Molecular Probes, Eugene Oreg.) by incubating the islets for 25 min at 37° C. in Krebs solution supplemented with 2 mM glucose (KRB2), containing 5 μM Fura-2/AM. After loading, the islets were placed into a temperature-controlled perfusion chamber (Medical Systems Inc, Paola, Kans.) mounted on an inverted epifluorescence microscope (TE-2000U, Nikon, Inc.) and perfused by a continuous flow (rate 2.5 mL/min) with 5% $CO_2$-bubbled KRB2 buffer at 37° C. (pH 7.4). Krebs buffer containing different glucose concentrations (5, 8, and 14 mM) was administered to the islets and resulting fluorescence followed for 15 min each, rinsing with KRB2 in between. Multiple islets were imaged with 10x-20x objectives for each sample. Fura-2 dual-wavelength excitation was set at 340 nm and 380 nm (excitation wavelengths), and fluorescence detected at 510 nm (emission wavelength). Fluorescence was analyzed using Metafluor/Metamorph imaging acquisition and analysis software (Universal Imaging Corporation, West Chester, Pa.) and images collected using a high-speed, high-resolution charge-coupled device (Roper Cascade CCD, Tucson, Ariz.). Estimation of $Ca^{2+}$ levels was accomplished using an in vivo calibration method. The percentage change of intracellular $Ca^{2+}$ between both groups was calculated by the maximum increase after glucose stimulation, minus the basal (2 mM glucose) $Ca^{2+}$ level for each group.

Intracellular calcium ion concentration was also assessed in these islet cells in the presence of tolbutamide, an inhibitor of $K^+$-ATP channels. In these experiments, tolbutamide was added to the perfusion media at a final concentration of 100 μM in Krebs perfusion media containing 2 mM glucose and used to perfuse islet cells in the absence of glucose stimulation over basal (2 mM glucose). These measurements were performed on islets as described above.

Islet cell function was also assessed for glucose-induced insulin secretion. Static glucose incubation was used to compare glucose induced insulin secretion (stimulation index, SI) between islets isolated in the presence or absence of PolySFH-P as described in Example 1. SI as used herein was defined by the ratio of stimulated versus basal insulin secretion. Briefly, for each experiment, groups of 5 hand-picked islets with similar size (approximately 100 μM) were placed in five different wells of a 12 well-plate (5 replicates), then pre-incubated with 1 mL of Krebs buffer at low glucose concentration (1.6 mM glucose final concentration) for 30 min, after which the supernatant was collected and discarded. Islets were then incubated for 1 hour in low glucose Krebs (1.6 mM glucose final concentration) at 37° C. and 5% $CO_2$, and supernatants were collected under a microscope taking care of not removing any islets from the well. The same step was repeated with addition of Krebs-high glucose solution (16.7 mM glucose final concentration) and incubation of the islets under these conditions for 90 min. Supernatants were collected and frozen at −20° C. for later measurement using an ELISA kit immunologically-specific for rat insulin (obtained from Mercodia, Uppsala, Sweden). All samples are measured in duplicates.

Isolation in the presence of $O_2$ created the potential for reactive oxygen species (ROS) to have injured the functional integrity of islet cells, particularly at the mitochondrial and cell membranes, which could be disrupted inter alia by ROS-peroxidation. Functional integrity of islet cells isolated in the presence or absence of Poly-SFH-P as disclosed in Example 1 was further assessed by analyzing mitochondrial membrane integrity. In these assays, mitochondrial membrane potential were assessed using the fluorescent dye Rhodamine 123 (Rh123), a lipophilic cation that integrates selectively into the negatively-charged mitochondrial membranes and can be used as a probe of mitochondrial transmembrane potential. In cells pre-loaded with Rh123, membrane potential increase (hyper-polarization), which occurs after glucose stimulation in functional islet cells, causes more Rh123 to be concentrated in the mitochondrial membrane, leading to aggregation of dye molecules and a decrease (quenching) of the fluorescence signal. Rh123 was used as previously described. (Zhou et al., 2000, *Am J Physiol Endocrinol Metab* 278: E340-E351). Briefly, islets were incubated for 20 min at 37° C. in Krebs solution containing 2 mM glucose and supplemented with 10 μg/mL Rh123 (Molecular Probes, Eugene, Oreg.), then placed into a temperature-controlled perfusion chamber (Medical Systems Inc.) mounted on an inverted epifluorescence microscope (TE-2000U, Nikon Inc, Melville, N.Y.) The islets were perfused with a continuous flow (rate 2.5 ml/min) of 5% $CO_2$-bubbled Krebs buffer at 37° C. (pH 7.4). Islets were then stimulated with 14 mM glucose and the changes in fluorescence measured for 15 min after glucose stimulation. Rh123 fluorescence was determined using 540 as excitation wavelength and 590 as emission wavelength, and images collected with a charged coupled device camera (Roper Cascade CCD). Data were normalized to the average fluorescence intensity recorded during a five-minute period prior to glucose stimulation. The percentage change in fluorescence intensity between both islet isolation groups (i.e., isolated in the presence or absence of Poly-SFH-P) was calculated as the maximum reduction in fluorescence intensity after 14 mM glucose stimulation, minus the basal fluorescence intensity for each group.

In addition, Rh123 was used to assay islet cells for changes in mitochondrial morphology. In these assays, islets from PolySFH-P and control groups were incubated for 15 min. in Krebs buffer containing 2.5 μM Rh123 and visualized using a Carl Zeiss LSM 510 confocal microscopy equipped with 60× water immersion objective. The 488 nm line from an argon-krypton laser used for excitation and Rh123 emission was detected through an LP 505 filter. The intensity and the distribution of fluorescence were used to morphologically characterize mitochondrial integrity in these islet cells.

Another assay of ROS-caused injury was assessment of oxidative stress by assaying reduced glutathione (GSH) levels. These assays were performed on islet cells 12 hours post-isolation using the monochlorobimane (mcbm) method (Avila et al., 2003, *Cell Transplant* 12: 877-881). Briefly, 500 islets were cultured for 30 min at 37° C. in one well of a 12 well-plate in 5 mL CMRL culture medium containing 10 μL mcbm (a final concentration of 50 mM) (Molecular Probes). Islets were collected, washed with phosphate buffered saline (PBS) at pH 7.5, resuspended in 500 μL of 50 mM TRIS buffer containing 1 mM EDTA and then sonicated. The sonicated islet cell mixture was the centrifuged to clear the supernatant of debris and the fluorescence from the cleared supernatant detected using a fluorescence plate reader (GENios, Tecan US Inc., Durham, N.C.) with an excitation wavelength of 380 nm and an emission wavelength of 470 nm.

Cell membrane damage from lipid peroxidation by ROS was used as a marker of oxidative injury. The extent of lipid peroxidation in islets isolated in the presence or absence of Poly-SFH-P as disclosed in Example 1 was determined by detecting malondialdehyde (MDA), a product of lipid peroxidation. MDA levels were assessed using thiobarbituric acid (TBA) according to the method of Yagi (1998, *Methods Mol Biol* 108: 101-106). Briefly, a reaction mixture was prepared containing 0.1 M HCl, 0.67% TBA, 10% phosphotungstic acid and 7% sodium dodecylsulphate (SDS) (all obtained from Sigma). 500 islets were sonicated in 700 μL PBS into a cell lysate. After centrifugation at 15,000 rpm to clear the lysate of debris, 500 μL of the supernatant were extracted and mixed with 875 μL of the reaction mixture, then boiled at 95-98° C. for 1 hour. After this process, samples were cooled and mixed with 750 μL of n-butanol in order to extract MDA and avoid interference of other compounds. After a brief centrifugation, 100 μL of this supernatant were extracted and fluorescence assessed in duplicate on a 96 well plate with a fluorometer (GENios, Tecan US Inc. Durham, N.C.) at an excitation wavelength of 530/25 and an emission wavelength of 575/15. Samples were assayed in comparison with MDA standards (obtained from Sigma) prepared at different concentrations (2, 4, and 8 mM).

The results of these experiments are shown in FIGS. 1-9. FIG. 1 shows the results of perfusion of rat pancreata with PolySFH-P on islet yield, which did not have a significant impact on post-isolation islet yields when compared to the control group (207±33 vs. 172±32 islets/rat respectively, p=0.46).

The results on islet viability, on the other hand, surprisingly showed that viability was significantly increased in isolates prepared in the presence of PolySFH-P compared with the control collagenase/RPMI 1640 media without PolySFH-P (FIG. 1).

In Caspace-3 experiments to assess the extent to which cell viability was compromised by apoptosis, isolated islets from PolySFH-P perfused pancreata showed fewer apoptotic cells compared to the control (FIG. 2) as detected by lower caspase 3 activity.

Figure 4:
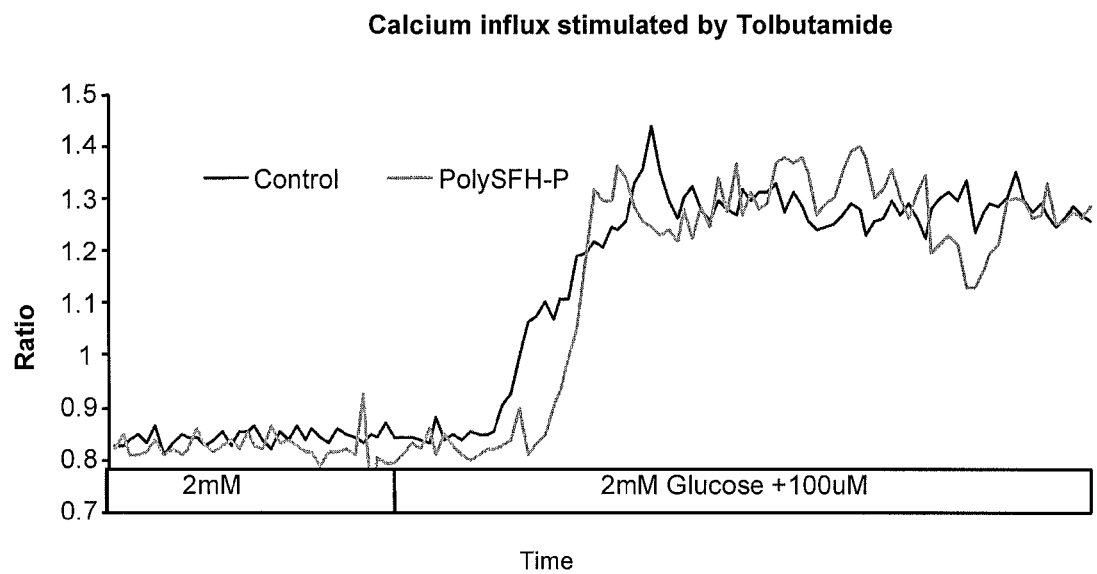
FIG. 4A shows changes in ratio-metric values (Fura 2/AM) as a measurement of intracellular calcium levels in two representative islets under basal glucose (2 mM) conditions after the addition of Tolbutamide (100 μM).
FIG. 4B shows the area under the curve (AUC) for intracellular calcium levels under basal glucose concentration (2 mM) in islets from both groups after the addition of Tolbutamide (100 μM). (n=25 islets per group), represented as mean±SEM. p=0.183.
Figure 4:
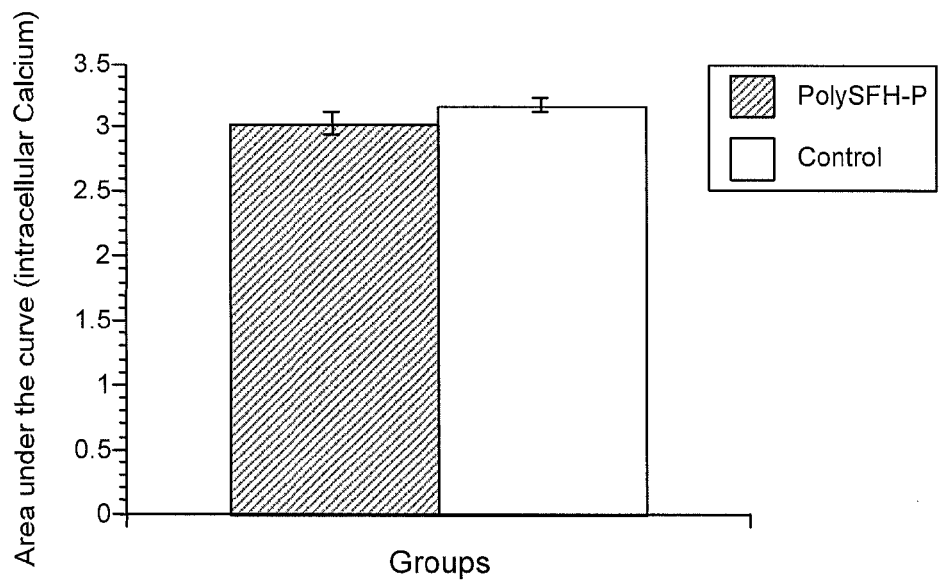

Turning to experiments directed at assessing the impact of islet isolation in the presence of PolySFH-P on islet cell function, improved islet responsiveness to glucose was shown by increased intracellular $Ca^{2+}$ levels in islets after stimulation with glucose at different concentrations (FIG. 3A). In all three concentrations (5, 8, 15 and 14 mM) of glucose tested, PolySFH-P-treated islets demonstrated significantly higher intracellular $Ca^{2+}$ values than control in a dose-response manner (FIG. 3B). Further, addition of tolbutamide (an inhibitor of ATP-dependent $K^+$ channels) showed that when mitochondrial ATP regulation in these channels was by-passed, there was no significant difference in intracellular $Ca^{2+}$ levels between both groups (FIGS. 4 A and B).

Figure 5:
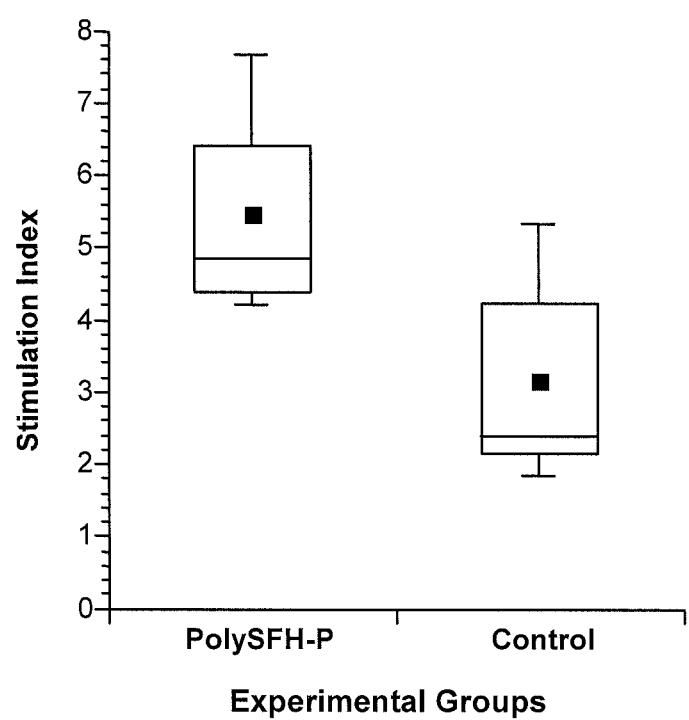
FIG. 5 shows insulin secretion of islets in response to glucose challenge, expressed as a stimulation index (SI), represented as mean±SEM. PolySFH-P isolations (n=5), control isolations (n=5), *p=0.03.

Finally, insulin secretion in response to glucose stimulation was significantly increased in islet cells isolated from rat pancreata in the presence of PolySFH-P compared to the control group (FIG. 5).

Figure 6:
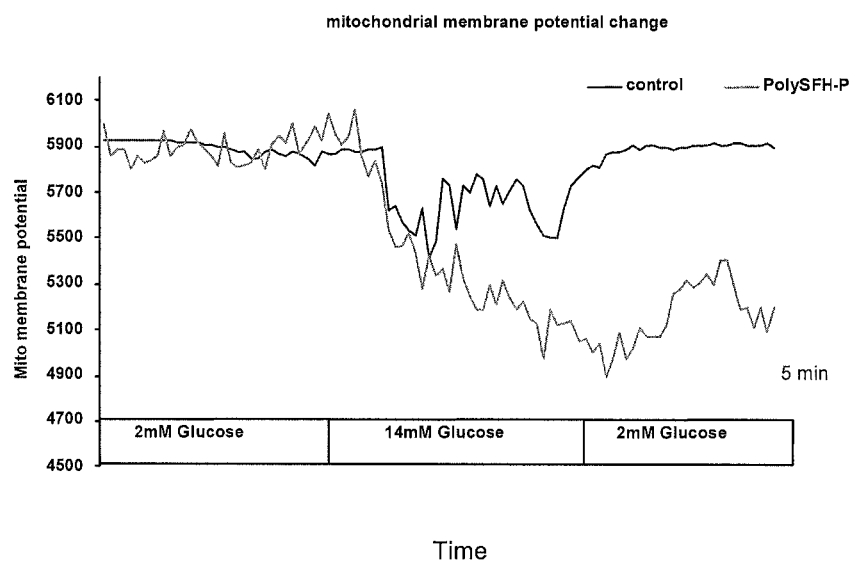
FIG. 6A shows levels of Rhodamine 123 (Rh123)-fluorescence outside the mitochondrial inner membrane in two representative islets under basal (2 mM) and glucose-stimulated conditions (14 mM). A gradual decrease in fluorescence represents the incorporation of Rh123 into the membrane as an indirect measurement of membrane potentials.
FIG. 6B shows the percentage change in mitochondrial potentials in islets from PolySFH-P and control groups, (n=25 islets per group), represented as mean±SEM. p<0.05.
Figure 6:
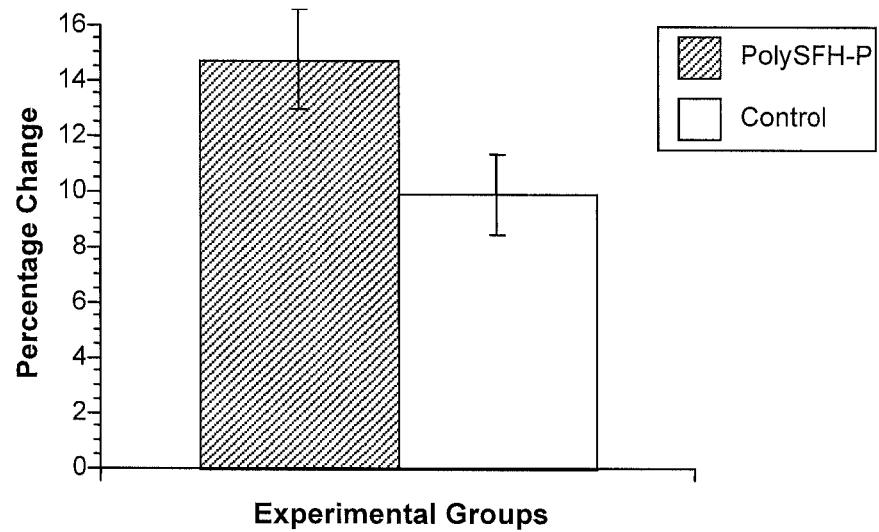
Figure 7:
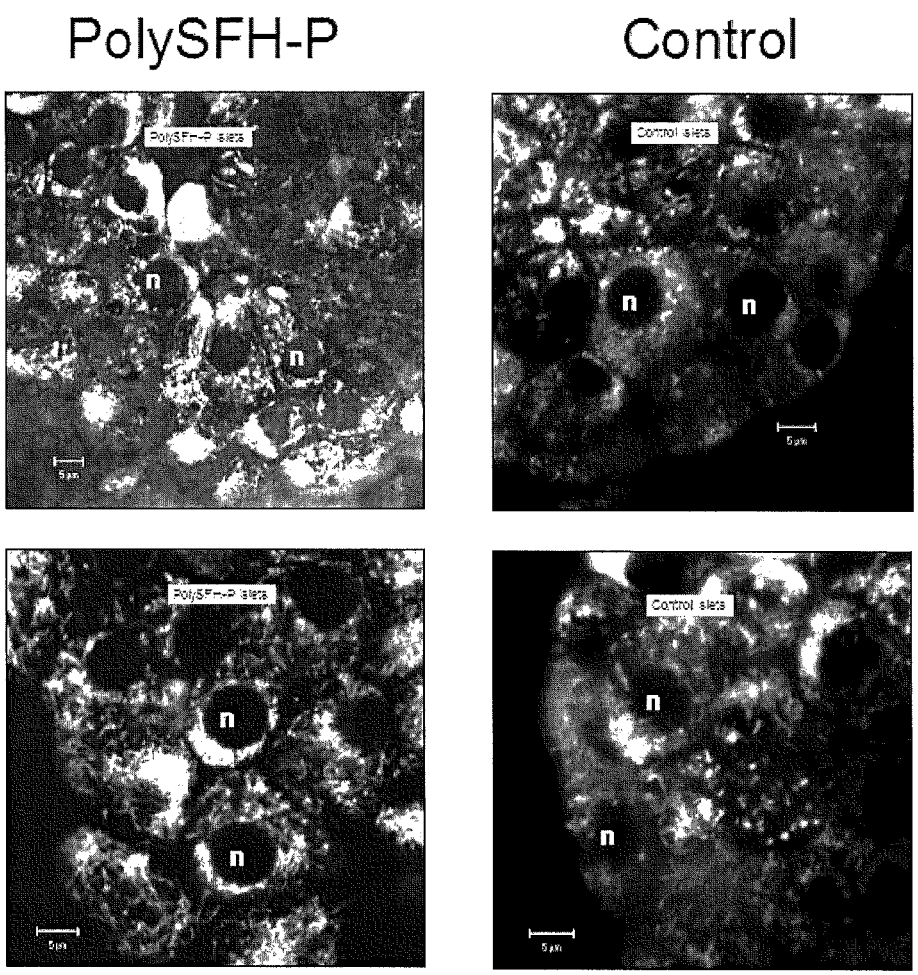
FIG. 7 shows mitochondrial morphology. Mitochondria were stained with Rh123 dye. Two representative images (confocal reconstructions) from individual islets from PolySFH-P and control groups are shown. Images are maximum intensity projections, 1 μm slice thickness. Cell nuclei in the islets are identified with the letter "n". Mitochondrial morphology and distribution around the nuclei appear superior in the PolySFH-P group than in the control. Contrast has been balanced to reveal details of mitochondrial morphology. Scale bar is 5 μm.

The results of experiments to assess whether ROS were present during islet isolation and to what extent these species caused oxidative damage to the islet cells are shown in FIGS. 6 and 7. Measurements of mitochondrial membrane potential indicated a better functional integrity of PolySFH-P islets than in the control group as shown by an increased percentage of the change (decrease) in Rh123 fluorescence, representative of undamaged electrochemical potential as a response to glucose stimulation (14 mM) (FIGS. 6A and 6B). In addition, morphological assessment of mitochondria in islets from the control group appeared swollen and fragmented, showing decreased staining with Rh123 around the nuclei with loss of the continuity of the staining. In contrast, PolySFH-P treatment showed improved islet cell mitochondrial morphology, with reduced swelling and fragmentation and increased staining around the nuclei (FIG. 7). These results are consistent with islet isolation in the presence of PolySFH-P showing less ROS-generated oxidative damage that in the control group isolated in the absence of PolySFH-P.

Whether $O_2$ delivery by PolySFH-P increased oxidative stress or injury was established by assaying GSH and MDA levels in islet cells isolated as disclosed in Example 1. Oxygenated PolySFH-P did not decrease glutathione levels (7.1±2.9 nmol/mg protein for PolySFH-P and 6.8±2.4 for control; p=0.93). Similarly, lipid peroxidation as measured by MDA levels was not significantly different between PolySFH-P and control group (1.8±0.9 nmol/mg protein vs. 6.2±2.4, respectively; p=0.19) indicating the there was no increased oxidative stress by the presence of higher $O_2$ levels.

The foregoing observations indicated that, surprisingly, intraductal perfusion of ischemic pancreata with PolySFH-P improved islet viability and function associated with maintenance of mitochondrial integrity, and that isolating pancreatic islets in the presence of PolySFH-P did not lead to increased oxidative stress in isolated islets.

These results illustrate significant advantages in using PolySFH-P in isolating pancreatic islets. These results demonstrated that mitochondria, which are a major contributor to apoptotic cell death under ischemic conditions, maintain improved function and integrity in the presence of oxygenated PolySFH-P. Higher $O_2$ availability to PolySFH-P-treated islets was shown by higher $O_2$ tensions in the perfusion media compared to the control. The availability of $O_2$ substrate for mitochondria may be responsible for the improved viability observed in islets from the PolySFH-P group. Islets are exposed to significant oxidative stress during the islet isolation and transplantation procedure. Surprisingly, increased $O_2$ provided in the form of oxygenated PolySFH-P did not result in significant production of ROS as assessed by analysis of mitochondria, both structurally and functionally as shown above. Indeed, the results shown above support the conclusion that mitochondrial function and integrity were improved by oxygenated PolySFH-P treatment, leading to both improved glucose-stimulated insulin secretion and decreased cell death.

The results shown above indicated that increased $O_2$ availability resulting from the use of oxygenated PolySFH-P protected islets from apoptosis, measured by lower levels of caspase-3 than in the control group. This result is consistent with the observation that hypoxia has been shown to initiate apoptosis, mainly through the release of mitochondrial mediators into the cytosol. Mitochondrial functional integrity was shown to be superior in PolySFH-P-treated islets with improved membrane electrochemical potential in response to glucose stimulation. Functional integrity was complemented by the conservation of mitochondrial structure in the PolySFH-P-treated islets, determined by less swelling and more elongated mitochondria. Enhanced mitochondrial staining, representative of improved perinuclear localization in the PolySFH-P-treated islets, was also observed.

The foregoing results also indicate that in vitro function of isolated islets was improved by intraductal administration of PolySFH-P to the ischemic pancreas. Higher stimulation indices were obtained in PolySFH-P-treated islets compared to the control in response to a static glucose challenge. The enhanced function for PolySFH-P treated islets was supported by higher intracellular $Ca^{2+}$ levels in response to glucose. These results demonstrate that the capacity of islet mitochondria to increase cytosolic $Ca^{2+}$, necessary for insulin secretion in beta cells, is greater in islets isolated in the presence than in the absence of oxygenated PolySFH-P. The specificity of this improvement was shown in experiments where islets were incubated in the presence of tolbutamide, a $K^+$-ATP channel inhibitor. Under these conditions, cells depolarize and raise calcium levels, directly promoting insulin secretion. After the addition of tolbutamide, intracellular $Ca^{2+}$ response to glucose was similar between both groups. These results suggest that the provision of $O^2$ by PolySFH-P protected the mitochondrial pathway in the process of insulin secretion in response to glucose.

These in vitro results all supported the conclusion that pancreatic islets isolated in the presence of oxygenated PolySFH-P were structurally and functionally superior to islets isolated without oxygenated PolySFH-P.

EXAMPLE 5

In Vivo Assessment of Islet Yield, Viability, and Function

Islet function was assessed in vivo by transplantation under the kidney capsule of diabetic athymic nude mice (Harlan Industries), using animals treated as set forth in Example 1 with the exception that these animals were housed and surgeries performed under a laminar flow hood located in "barrier" rooms to prevent adventitious infection.

Diabetes was induced in these animals by a single intraperitoneal (IP) injection of streptozotocin (Sigma) at a dose of 220 mg/kg body weight. Diabetes was considered induced in treated animals after three or more non-fasting blood glucose levels of >300 mg/dL taken from the tail vein, which generally occurred after a maximum of 72 hours post injection.

For transplantation, animals were anesthetized by isoflurane inhalation using a vaporizer and masks (Viking Medical). In these experiments, islets were transplanted without culture fresh after isolation. 250 islets from PolySFH-P/RPMI solution-treated pancreata (PolySFH-P) or RPMI 1640 medium-treated pancreata (Control) were transplanted into each mouse under the left kidney capsule as described in Oberholzer et al. (1999, *Immunology* 97:173-180). It was expected using this procedure that transplantation of 250 ischemic rat islets would reverse diabetes in less than 50% of recipients. Successful transplantation was defined by reduction of glycemia to below 200 mg/dL. Normoglycemic recipients underwent graft-bearing nephrectomy 5-7 weeks post-transplantation. Return to hyperglycemia was interpreted as indirect proof of islet graft function rather than spontaneous recovery of the native pancreas.

Graft function was also assessed by the lag period required to achieve normoglycemia, using an Intraperitoneal Glucose/Arginine tolerance test (IPG/ATT) one week post-transplantation. Briefly, in these assays glucose (at 2 mg/kg body weight) and arginine (3 mg/kg) were injected intraperitoneally (IP) in 0.5 cc using a representative sample of randomly selected euglycemic animals (n=5 for PolySFH-P and n=3 for Control; in the Control group only 4 animals achieved normoglycemia). Blood glucose levels were detected by tail puncture at serial time-points (0, 5, 15, 30, 45 and 60 minutes) after injection.

The results of these experiments were evaluated statistically, using Student's t test and Pearson Chi-Square test, where p values <0.05 were regarded as statistically significant.

Figure 8:
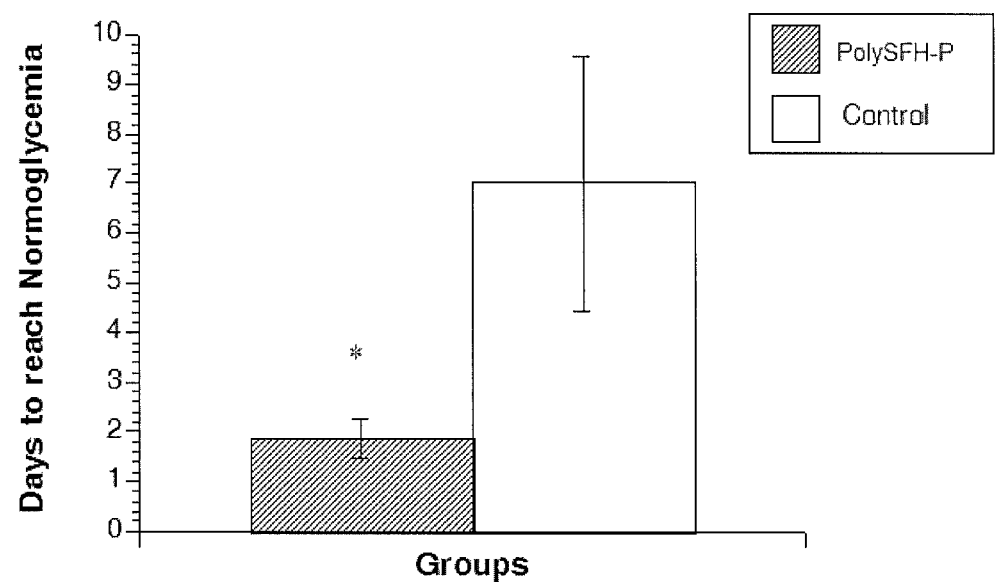
FIG. 8 shows the number of days (lag time) to reach normoglycemia after islet transplantation in mice. PolySFH-P mice (n=6) and control mice (n=4). *p=0.02.
Figure 9:
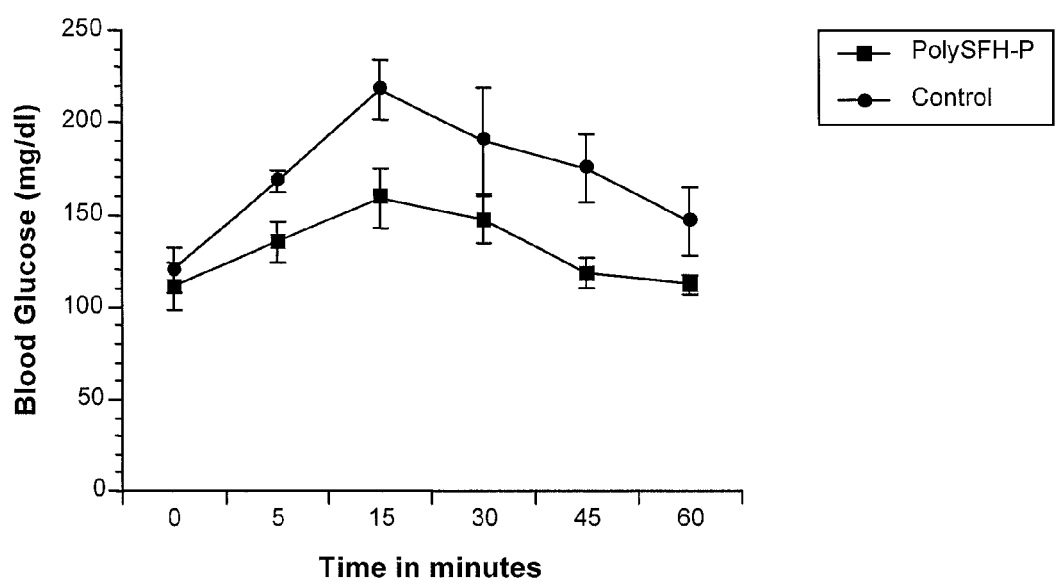
FIG. 9 shows the results of an Intraperitoneal Glucose/Arginine Tolerance Test (IPG/ATT) in a representative sample of mice that reached normoglycemia after transplantation with islets from PolySFH-P (n=5) and control (n=3). Values indicate mean blood glucose levels±SEM. p=0.03.

The results of the foregoing experiments revealed that the percentage of cured mice transplanted with PolySFH-P or Control islets was similar (6 out of 10 and 4 out of 9 respectively, p=0.4). Surprisingly, mice transplanted with islets treated with PolySFH-P achieved normoglycemia and reversed diabetes in a significantly shorter time than the mice transplanted with islets from the Control group (FIG. 8). Moreover, the mice receiving PolySFH-P-treated islets showed better graft function with lower glucose levels during IPG/ATT (FIG. 9).

These results indicated that PolySFH-P perfusion of the ischemic rat pancreas improved islet graft function in vivo, as shown by a better response to IPG/AT stress test and a shortened lag time to reach normoglycemia after transplantation. These in vivo results confirmed the improved function of PolySFH-P-treated islets observed in vitro.

In order to determine the effect of PolySFH-P perfusion specifically on the beta cell population, fractional beta cell viability was assessed using the method of Ichii et al. (2005, *Am J Transplant* 5:1635-1645). This method involved assessing cell membrane stability and mitochondrial membrane stability of beta and non-beta cells. In these experiments, islets were dissociated and the cells staining with the following dyes: 7-aminoactinomycin D (7aad, specific for cell membrane stability), teramethylrhodamine ethyl ester (TMRE, mitochondrial membrane stability) and Newport Green (NG, wherein NG high populations were beta cells and NG low populations were non-beta cells). A single cell suspension was created by incubating 1000 islets per condition in 2 mL Accutase (Innovative Cell Technologies Inc. San Diego) for 7 minutes at 37° C. followed by gentle pipetting. Cells were then incubated with 1 uM Newport green PDX; (Invitrogen, Molecular Probes) and 100 ng/mL TMRE (Invitrogen, Molecular Probes) in PBS for 30 min at 37° C. After washing with PBS, cells were stained with 5 ug/mL 7AAD (Invitrogen, Molecular Probes). The cells were analyzed using Cell Quest software and the LSR by Becton Dickinson (Mountainview, Calif.). Gating for NG was performed by side scatter and FL1.

Figure 10:
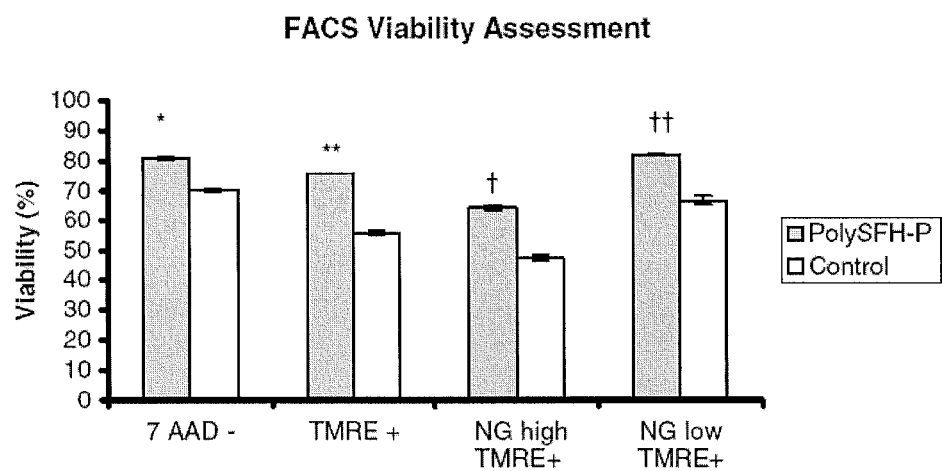
FIG. 10 is a graph showing viability staining specific for beta and non-beta cells from isolated islet cell populations. Cells were assayed for cell membrane stability (7aaD), mitochondrial membrane stability (TMRE) in beta cells (gating the Newport Green (NG) high population) versus non-beta cell (NG low population), n=3 per group. *p<0.001; **p<0.001; †p<0.001; ††p<0.001.

The results of these experiments are shown graphically in FIG. 10. PolySFH-P improved integrity of both beta and non-beta cells. Fractional islet cell viability assessment indicated that beta cells were more vulnerable to ischemic damage than non-beta cells in the islets, and thus benefited to a greater extent from the presence of oxygenated PolySFH-P in the culture media.

Although certain presently preferred embodiments of the application have been described herein, it will be apparent to those of skill in the art to which the application pertains that variations and modifications of the described embodiment may be made without departing from the spirit and scope of the application.

Accordingly, it is intended that the application be limited only to the extent required by the following claims and the applicable rules of law.

What is claimed is:

1. A method of isolating pancreatic islets from a pancreatic tissue in a mammal, comprising the steps of:
    a) contacting the pancreatic tissue of the mammal that includes the pancreatic islets a solution that includes polymerized hemoglobin derived from mammalian blood and a proteolytic enzyme; wherein the solution includes a concentration of between 5 and 15 g/dL of polymerized hemoglobin; and thereafter
    b) recovering the pancreatic islets from the mammalian tissue, thereby isolating the pancreatic islets.

2. The method of claim 1, wherein the tissue is human pancreatic tissue and the polymerized hemoglobin is derived from human blood.

3. The method of claim 2, wherein the polymerized hemoglobin derived from human blood is pyridoxylated.

4. The method of claim 2, wherein the solution is oxygenated.

5. The method of claim 2, wherein the contacting step is achieved by intraductal administration.

6. The method of claim 2, further including the step of washing the pancreatic islets with a cell culture medium to produce washed pancreatic islets.

7. The method of claim 6, further including the step of purifying the washed pancreatic islets by density gradient centrifugation.

8. The method of claim 1, wherein the solution further includes a cell culture medium.

9. The method of claim 8, wherein the cell culture medium is RPMI.

10. The method of claim 1, wherein the proteolytic enzyme is collagenase.

11. The method of claim 1, wherein the solution further includes a buffer.

12. The method of claim 1, wherein the polymerized hemoglobin is derived from human blood and is pyridoxylated.

13. The method of claim 12, wherein the solution further includes a cell culture medium.

14. The method of claim 13, wherein the proteolytic enzyme is collagenase and the cell culture medium is RPMI.

15. The method of claim 14, wherein the solution is oxygenated.

16. The method of claim 1, wherein the solution is oxygenated.

* * * * *

UNITED STATES PATENT AND TRADEMARK OFFICE
CERTIFICATE OF CORRECTION

| | |
|---|---|
| PATENT NO. | : 9,657,271 B2 |
| APPLICATION NO. | : 13/755091 |
| DATED | : May 23, 2017 |
| INVENTOR(S) | : Jose Oberholzer and Marc Doubleday |

Page 1 of 1

It is certified that error appears in the above-identified patent and that said Letters Patent is hereby corrected as shown below:

On the Title Page

In the Related to U.S. Application Data (60) section, in the fifth line, delete "which".

In the Specification

After the section Related to U.S. Application Data (60), insert a new paragraph to read:
-- GOVERNMENT SUPPORT
This invention was made with government support under grant number U42 RR023245 from the National Institutes of Health. The government has certain rights in the invention. --.

In the Claims

In Claim 1, Column 20, Line 13, after "islets" insert -- with --.

Signed and Sealed this
Seventeenth Day of October, 2017

Joseph Matal
*Performing the Functions and Duties of the
Under Secretary of Commerce for Intellectual Property and
Director of the United States Patent and Trademark Office*